(12) United States Patent
Blevis

(10) Patent No.: US 8,115,171 B2
(45) Date of Patent: Feb. 14, 2012

(54) GAMMA CAMERA FOR PERFORMING NUCLEAR MAMMOGRAPHY IMAGING

(75) Inventor: Ira Blevis, Zichron Yaakov (IL)

(73) Assignee: General Electric Company, Schenectady, NY (US)

( * ) Notice: Subject to any disclaimer, the term of this patent is extended or adjusted under 35 U.S.C. 154(b) by 169 days.

(21) Appl. No.: 12/493,407

(22) Filed: Jun. 29, 2009

(65) Prior Publication Data

US 2010/0329419 A1 Dec. 30, 2010

(51) Int. Cl.
*G01T 1/161* (2006.01)
*A61B 6/04* (2006.01)

(52) U.S. Cl. ................ 250/363.02; 378/37

(58) Field of Classification Search ........... 250/363.01, 250/363.05, 363.052, 363.02, 370.09; 378/37
See application file for complete search history.

(56) References Cited

U.S. PATENT DOCUMENTS

| | | | |
|---|---|---|---|
| 5,519,221 A | 5/1996 | Weinberg | |
| 5,691,538 A | 11/1997 | Ohike et al. | |
| 5,811,813 A | 9/1998 | Maor | |
| 5,961,457 A | 10/1999 | Raylman et al. | |
| 6,055,450 A * | 4/2000 | Ashburn | 600/431 |
| 6,731,966 B1 | 5/2004 | Spigelman et al. | |
| 6,794,653 B2 * | 9/2004 | Wainer et al. | 250/363.01 |
| 2002/0148970 A1 | 10/2002 | Wong et al. | |
| 2003/0197127 A1 | 10/2003 | Wainer et al. | |
| 2007/0164224 A1 | 7/2007 | Hefetz | |
| 2007/0223651 A1 * | 9/2007 | Wagenaar et al. | 378/37 |
| 2008/0242979 A1 | 10/2008 | Fisher et al. | |
| 2010/0177866 A1 * | 7/2010 | Shibuya | 378/20 |

FOREIGN PATENT DOCUMENTS

WO WO-2008/073897 A2 6/2008

OTHER PUBLICATIONS

Rhodes et al.;"Molecular Breast Imaging: A New Technique using Technetium Tc 99m Scintimammography to Detect Small Tumors of the Breast";Mayo Clin Proc;Jan. 2005;80(1):24-30.
Garibaldi F et al, "A novel high resolution and high efficiency dual head detector for molecular breast imaging" Nuclear Science Symposium Conference Record, Oct. 19, 2008, pp. 5647-5649.
Madhav P et al, "Evlaution of tilted cone-beam CT orbits in the development of a dedicated hybrid mammotomography", Physics in Medicine and Biology, Part 54, No. 12, Jun. 21, 2009, pp. 3659-3676.
Roberts J et al, "The effect of acquisition interval and spatial resolution on dynamic cardiac imaging with a stationary SPECT camera; Dynamic cardiac imaging using a stationary SPECT camera", Physics in Medicine and Biology, Part 52, No. 15, Aug. 7, 2007, pp. 4525-4540.
Unofficial English translation of NL Search Report and Written Opinion from NL Patent Application No. 2004957, Jun. 27, 2011.

* cited by examiner

*Primary Examiner* — David Porta
*Assistant Examiner* — Faye Boosalis
(74) *Attorney, Agent, or Firm* — The Small Patent Law Group; Dean D. Small

(57) ABSTRACT

A gamma camera for use in a molecular imaging system includes a housing, a cadmium zinc telluride (CZT) camera disposed within the housing, and at least one retractable wall coupled to the housing and adapted to secure an anatomy of interest in a field-of-view of the gamma camera. The gamma camera also includes a chamfered edge to enable the gamma camera to contact a second gamma camera when the gamma camera is positioned in an L-mode imaging configuration.

20 Claims, 17 Drawing Sheets

GAMMA CAMERA FOR PERFORMING NUCLEAR MAMMOGRAPHY IMAGING

BACKGROUND OF THE INVENTION

This invention relates generally to medical imaging systems, and more particularly to a system and method for performing nuclear mammography imaging.

Different systems and methods for performing mammography imaging are known. For example, one conventional imaging system is a film screen mammography imaging. This type of mammography imaging system uses transmitted x-rays to produce an image of the breast. During the imaging procedure, a compression force is applied to a breast to improve image quality by reducing a thickness of the breast thereby spreading the breast tissue over a larger area. The reduction in the breast thickness, and spreading the breast over a larger area, facilitate reading of the projection radiographs, because the amount of "overlapping structures" within the imaged breast is minimized in the projection radiograph. This type of mammography imaging may not perform satisfactory imaging in women with dense breasts. Moreover, some patients may experience discomfort due to the compression force applied to the breast and lower patient acceptance may result in missed examinations, thereby possibly increasing the patient's risk that a serious medical condition may not be detected in a timely fashion.

Another conventional imaging system utilizes diagnostic nuclear imaging to identify radionuclide distribution in a subject, such as a human patient. Typically, one or more radiopharmaceuticals or radioisotopes are injected into the subject. The imaging system includes conventional gamma detectors that are placed adjacent to a surface of the subject to monitor and record emitted radiation. The monitored radiation data is reconstructed and/or displayed into an image representation of the radiopharmaceutical distribution within the subject. Generally the spatial resolution of a gamma detector degrades with increasing distance between the imaged area/organ and the detector. Therefore, it is desirable to place the gamma detector as close as possible to the patient to facilitate minimizing the loss of image resolution. It is also desirable to place the detector so that only the breast and no other confounding structures are in the imaging field of view. However, the size of these conventional detectors allows only anterior-posterior imaging with sufficient proximity to the breast, and in this case the background activity from the thorax structures including the heart degrade the sensitivity for finding small lesions of the breast.

Sometimes, small cameras are used with other views to overcome the previous problem. For example the medial lateral oblique view may be used or a compression force may be used. For example, when utilizing one compact imaging system to image a patient's breast, a compression force is applied to the breast to secure the breast during imaging process. However, similar to the film screen mammography imaging system the compression force may cause some patients to experience discomfort and may not schedule any future examinations, thereby possibly increasing the patient's risk that a serious medical condition may not be detected in a timely fashion. Thus there is a need to avoid compression in an imaging modality. Furthermore, there is a need to contain the breast in the field of view of dedicated compact cameras configured for breast imaging, for example in medial lateral oblique views where gravity may pull the breast out of the field of view.

BRIEF DESCRIPTION OF THE INVENTION

In one embodiment, a gamma camera is provided. The gamma camera includes a housing and a camera disposed within the housing. The gamma camera also includes a retractable wall or structure coupled to the housing, the retractable wall or structure being fully retracted into the housing or detachable from the housing, or otherwise removed from activation in a first imaging mode and extending from the housing or activated to retain the subject within the field of view in a different second imaging mode.

In another embodiment, another gamma camera is provided. The gamma camera includes a housing comprising a chamfered edge to enable the gamma camera to contact a different second gamma camera when the gamma camera is positioned in an L-mode imaging configuration, a cadmium zinc telluride (CZT) camera disposed within the housing, and at least one retractable wall coupled to the housing and adapted to secure an anatomy of interest in a field-of-view of the gamma camera.

In a further embodiment, a method of fabricating a gamma camera is provided. The method includes fabricating a housing that includes a first side, a second side, a third side, a fourth side, and an opening defined by the first, second, third, and fourth sides, installing a cadmium zinc telluride (CZT) camera within the housing opening, and installing at least one retractable wall within the housing, the retractable wall adapted to secure an anatomy of interest in a field-of-view of the gamma camera.

DETAILED DESCRIPTION OF THE INVENTION

Various embodiments of the invention provide a system and method for performing molecular imaging of an anatomy of interest. A technical effect of the various embodiments is to provide a molecular imaging system that is configured to perform imaging optionally in both an H-mode and an L-mode configuration. The molecular imaging system is also configured to identify tumors or lesions during or after an imaging examination and to facilitate performing a biopsy of the identified tumors or lesions in the anatomy of interest.

Figure 1A:
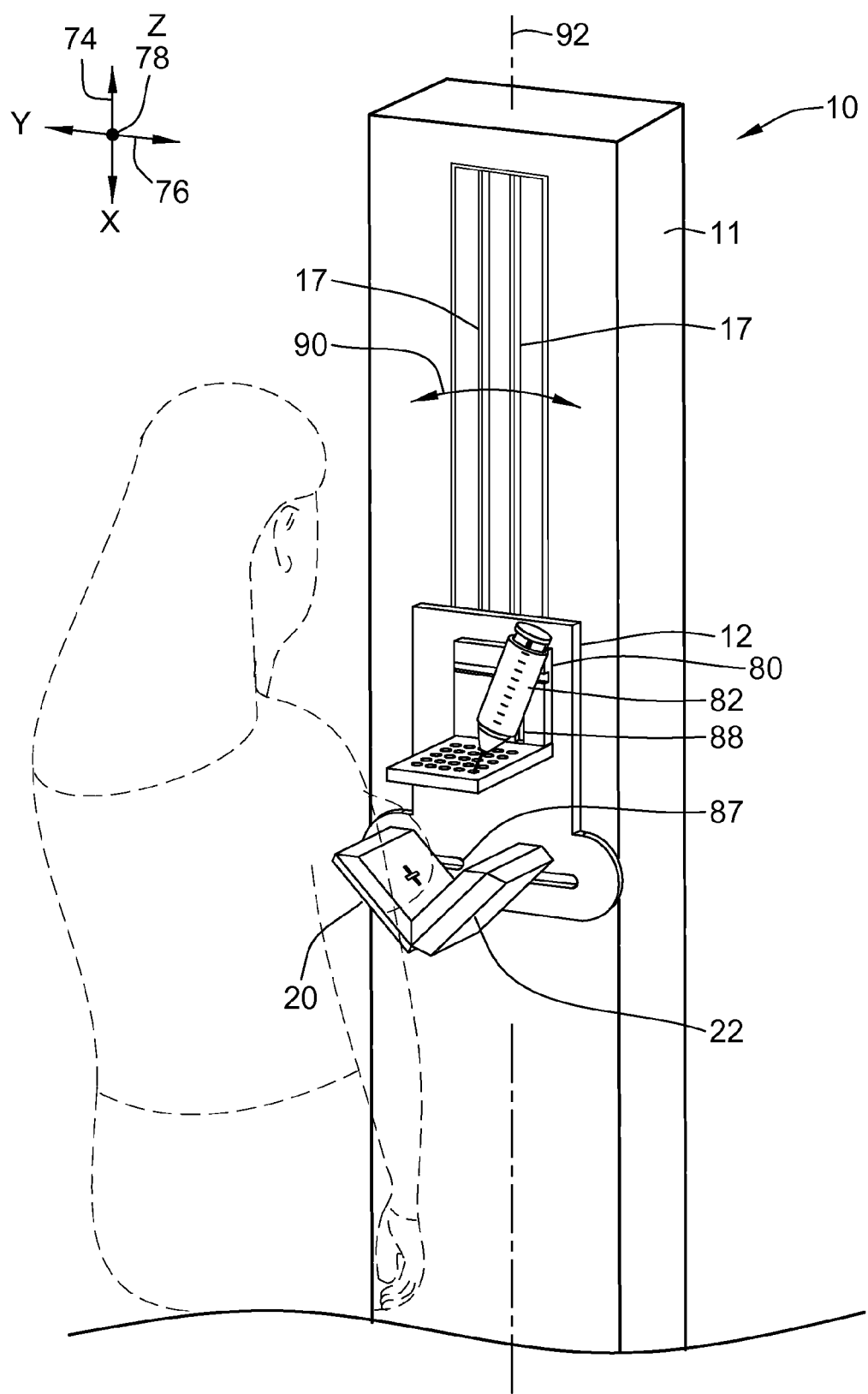
FIG. 1A is a front perspective view of an exemplary molecular imaging system in accordance with an embodiment of the present invention.
Figure 1B:
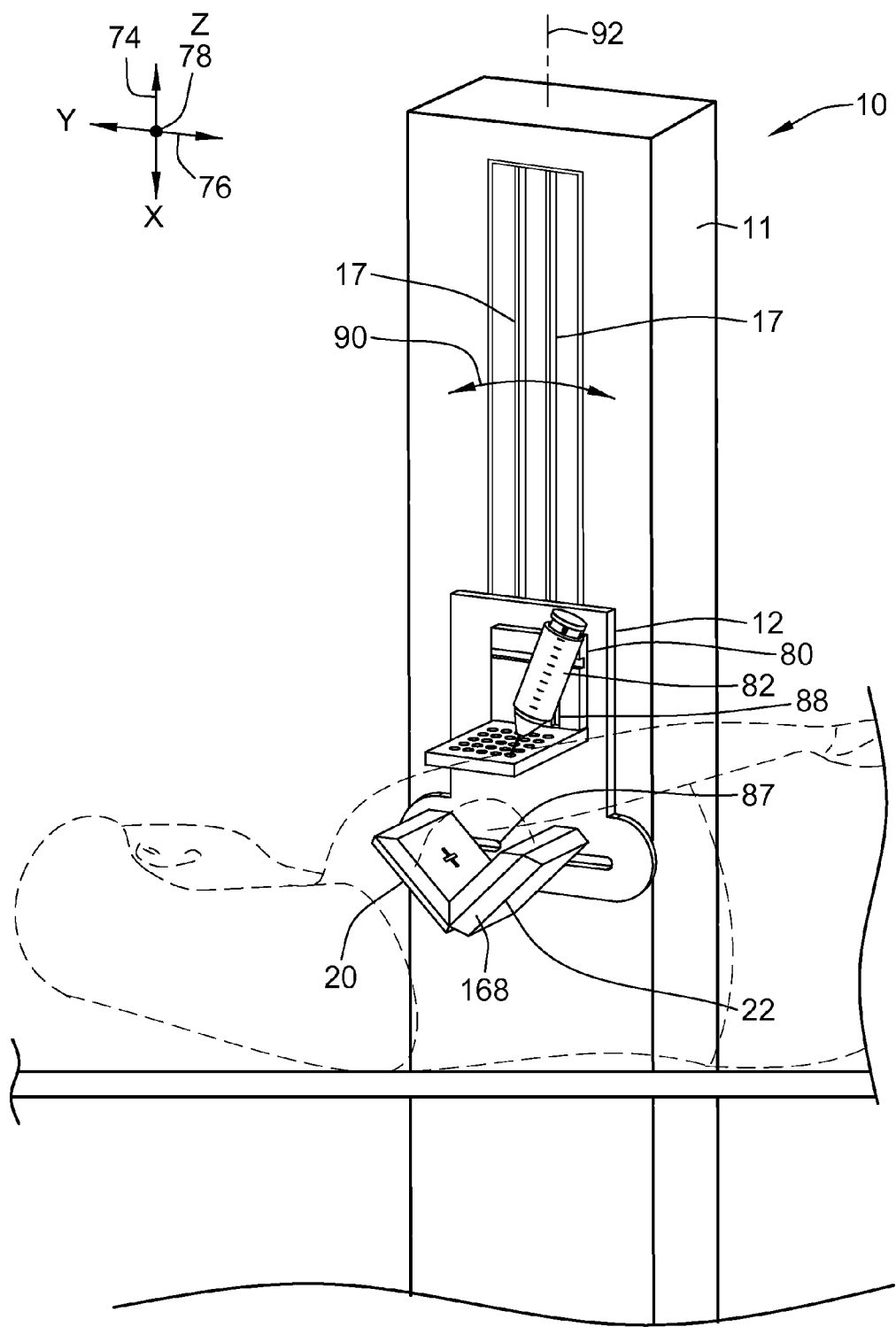
FIG. 1B is another front perspective view of an exemplary molecular imaging system shown in FIG. 1 including a patient positioned in a second imaging position in accordance with an embodiment of the present invention.
Figure 2:
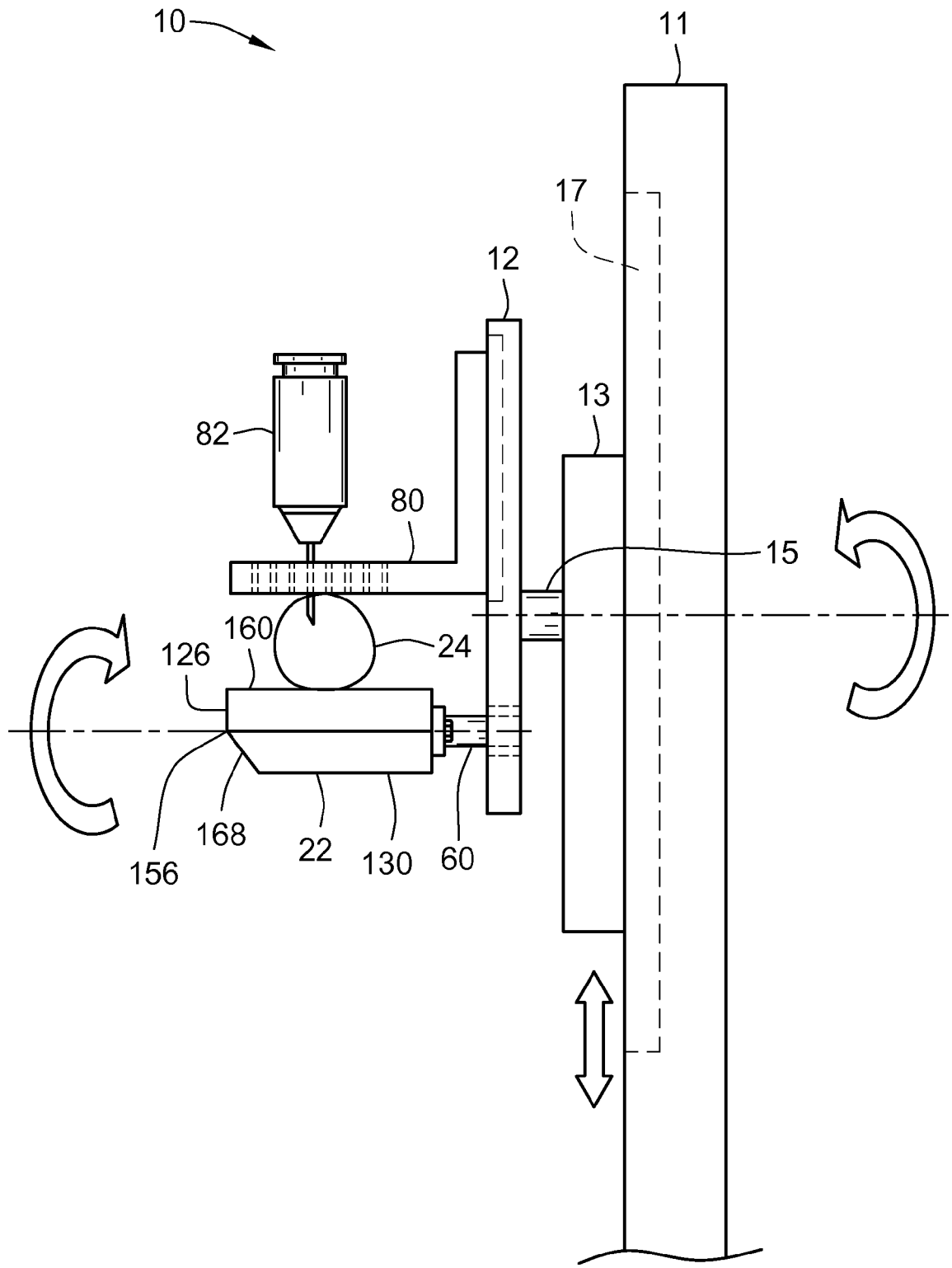
FIG. 2 is a side view of the imaging system shown in FIG. 1.

FIG. 1A is a front perspective view of an exemplary molecular imaging system 10 illustrating a patient positioned for imaging in a first imaging position. FIG. 1B is a front perspective view of the imaging system 10 illustrating a patient positioned for imaging in a second imaging position. FIG. 2 is a side view of the imaging system 10 shown in FIGS. 1A and 1B. In the exemplary embodiment, the molecular imaging system 10 is configured as a standalone molecular imaging system. The molecular imaging system 10 may be mounted stationary by coupling the system 10 to a floor. Optionally the system 10 may include wheels (not shown) to enable system 10 to be portable. The molecular imaging system 10 includes a housing 11 and a gantry 12 that is rotatably coupled to the housing 11 via a carriage 13. The imaging system 10 also includes a first gamma camera 20, a second gamma camera 22, and a biopsy needle positioning device 80 that are coupled to the gantry 12. To facilitate imaging in various configurations, the gantry 12 is rotatable around the housing 11.

Referring to FIG. 2, the gantry 12 is coupled to the housing 11 via the carriage 13. The gantry 12 is rotatably coupled to the carriage 13 via a pivot device 15. During operation, the carriage 13 is configured to move up and down along a pair of rails 17 to enable a patient to be imaged in a standing or sitting or bed position. Moreover, since the gamma cameras 20 and 22 and the biopsy needle positioning device 80 are rotatably coupled to the gantry 12 which is coupled to the carriage 13, the gamma cameras 20 and 22 and the biopsy needle positioning device 80 are also moveable along the pair of rails 17.

The gantry 12 is configured to pivot to a plurality of radial positions to position the gamma cameras 20 and 22 for imaging a patient. After the gantry 12 is positioned, the gantry 12 remains stationary during the imaging process as discussed below. Additionally, the first and second gamma cameras 20 and 22 are each positionable to perform imaging of an anatomy of interest 24 that is positioned between the first and second gamma cameras 20 and 22. During operation, the patient may be imaging by positioning the patient in a sitting position as shown in FIG. 1A. In this imaging position, the gamma cameras 20 and 22 are adjusted vertically until the height of the gamma cameras 20 and 22 are sufficient to enable the patient to place a breast on the gamma cameras 20 and 22. As shown in FIG. 1B the patient may also be imaging in a reclined or laying down position. In this case, the patient is positioned on a table in front of the gamma cameras 20 and 22. The gamma cameras 20 and 22 are then raised or lowered, via the gantry 12, the carriage 13, and the pair of rails 17, to enable the patient to place a breast on the gamma cameras 20 and 22. More specifically when the gamma cameras 20 and 22 are positioned at the proper imaging height, the patient is moved, via the movable table into the field of view of the gamma cameras.

Figure 3:
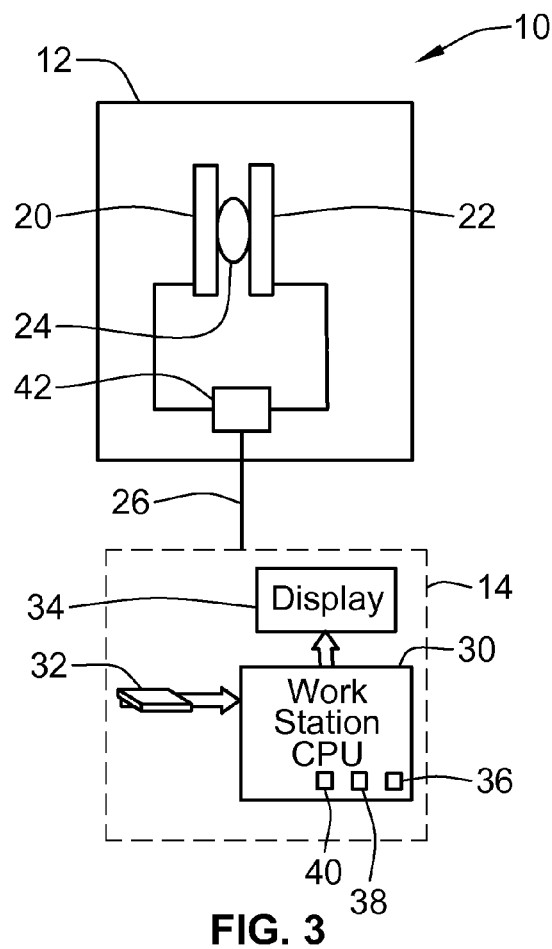
FIG. 3 is a schematic illustration of the exemplary molecular imaging system shown in FIGS. 1 and 2 in accordance with an embodiment of the present invention.

FIG. 3 is a schematic illustration of an exemplary workstation 14 that may be included with system 10 to control image reconstruction processes. In the exemplary embodiment, the operator workstation 14 is coupled to the housing 11, and thus is also coupled to the gantry 12 and the first and second gamma cameras 20 and 22. In one embodiment, the gantry 12 is coupled to the operator workstation 14 via a communication link 26 (e.g., a hardwired communication link or wireless communication link). Optionally, the operator workstation 14 may be constructed as part of the housing 11.

The operation of the molecular imaging system 10 is controlled by the operator workstation 14. As shown in FIG. 2, the operator workstation 14 includes a general purpose or a dedicated computer 30, an input device 32, and a display 34. The computer 30 may include a processor 36 and a memory device 38. The memory device 38 may be embodied as Random Access Memory (RAM) and/or Read Only Memory (ROM). The computer 30 further may include a storage device 40. The storage device 40 may be embodied as a hard disk drive or a removable storage such as a floppy disk drive, optical disk drive, USB memory and the like. The storage device 40 may also be other similar means for loading computer programs or other instructions into the computer 30.

As used herein, the term "computer" may include any processor-based or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer".

As discussed above, the operation of the molecular imaging system 10 is controlled from the operator workstation 14. More specifically the processor 36 executes a set of instructions that are stored in one or more storage elements, e.g. the memory device 38 and/or the storage device 40. The set of instructions instruct the processor 36 to perform various functions. One such exemplary function includes acquiring emission data from the gamma cameras 20 and 22 that is acquired from the anatomy of interest 24. More specifically, the set of instructions may include various commands that instruct the computer 30 as a processing machine to perform specific operations such as the methods and processes of the various embodiments of the invention. For example, one set of instructions may instruct the processor 36 to perform a scan of the anatomy of interest 24 using the first and second gamma cameras 20 and 22 to acquire emission data. Another set of instructions may instruct the processor 36 to transmit the emission data from the first gamma camera 20 to the communication link 26 via a communication link 42 and to transmit emission data from the second gamma camera 22 to the communication link 26 via the communication link 42. The set of instructions may further include instructions to instruct the processor 36 to utilize the emission data to reconstruct an image of the anatomy of interest 24 and display the reconstructed image on a display e.g. the display 34.

The set of instructions may be in the form of a software program. The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 4B:
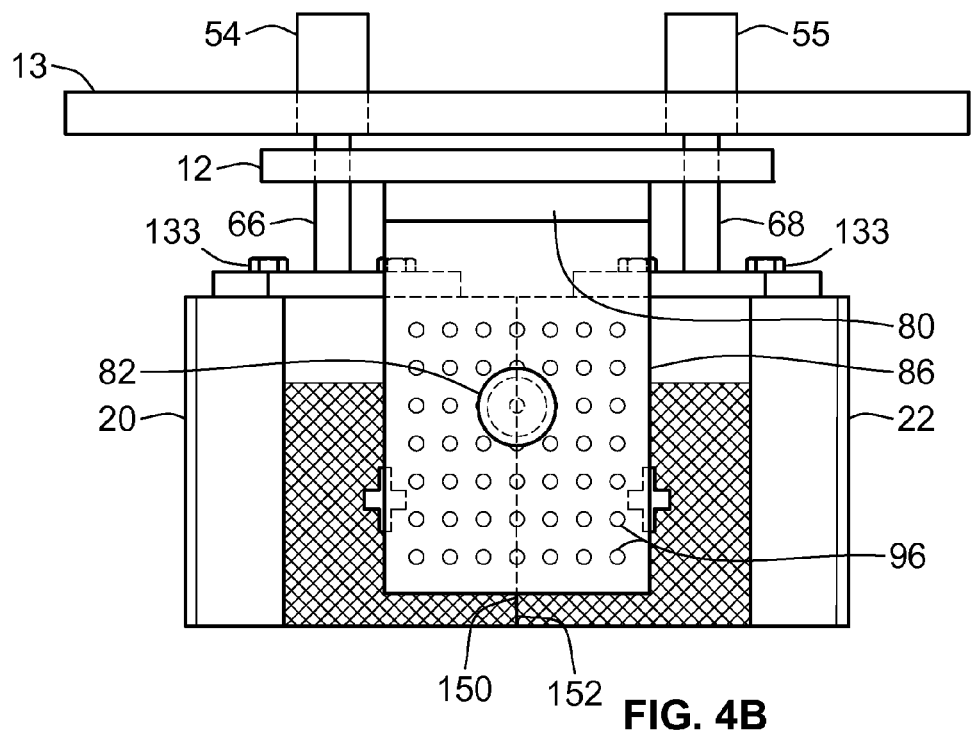
FIG. 4B is a top view of a portion of the molecular imaging system shown in FIG. 4A.
Figure 4A:
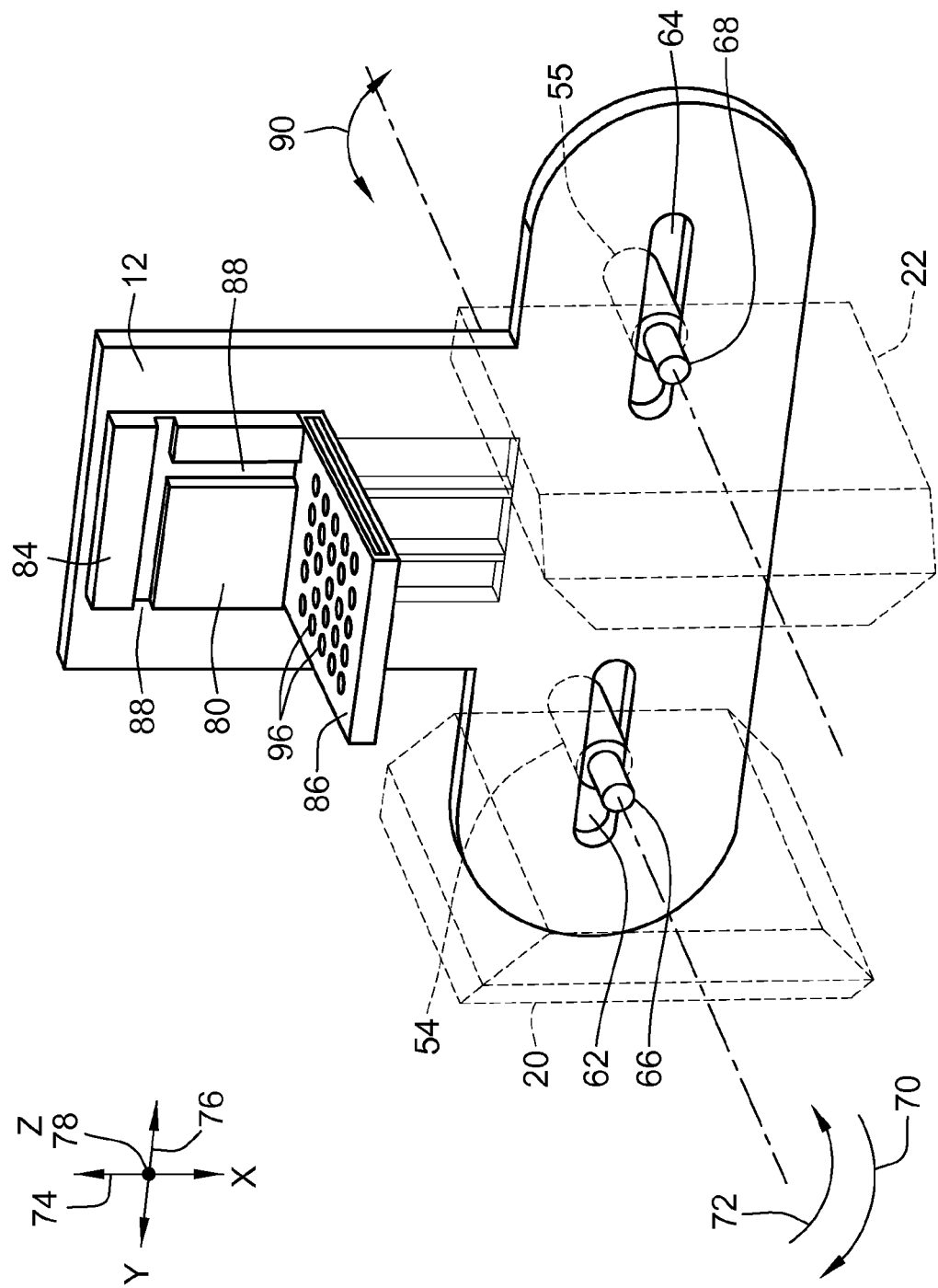
FIG. 4A is a front perspective view of a portion of the molecular imaging system shown in FIGS. 1 and 2 in accordance with an embodiment of the present invention.

During operation, the gamma cameras 20 and 22 are configured to be repositioned from a first operational positional to a second operational position. For example, FIG. 4A is a perspective view of the gantry 12 shown in FIGS. 1A and 1B including one such exemplary reposition device. FIG. 4B is a top view of the gantry 12 shown in FIGS. 1A and 1B including one such exemplary positioning device. As shown in FIG. 4A, in one exemplary embodiment, the gamma camera positioning device is embodied as a motor 54 that is coupled to and moves the gamma camera 20 around a radial axis. In this exemplary embodiment, the imaging system 10 also includes a motor 55 that is coupled to the gamma camera 22 and moves the gamma camera 22 around a radial axis. In another exemplary embodiment, the gamma cameras 20 and 22 may be repositioned manually by the operator. More specifically the gamma camera 20 and 22 may each be weighted and balanced and to enable the operator to disengage a mechanical or electromechanical clutch to permit manual repositioning of each respective gamma camera.

Referring again to FIG. 4A, the gantry 12 includes a first opening 62 and a second opening 64. Moreover, gamma camera 20 includes a mounting bracket 66 and gamma camera 22 includes a mounting bracket 68. The mounting brackets 66 and 68 are each coupled at a first end to the gamma camera 20 and 22, respectively. The mounting bracket 66 extends through the first opening 62 and the mounting bracket 68 extends through the second opening 64. The mounting brackets 66 and 68 are each anchored within the gantry 12 to enable each of the gamma cameras 20 and 22 to be repositioned. More specifically, the mounting brackets 66 and 68 enable each of the respective gamma cameras 20 and 22 to be positioned to perform imaging of the anatomy of interest 24.

In the exemplary embodiment, the mounting brackets 66 and 68 also enable the respective gamma cameras 20 and 22 to move in an X-direction 74, a Y-direction 76, and optionally in a Z-direction 78. Moving the gamma cameras 20 and 22 in the X-direction facilitates raising and lowering the gamma cameras 20 and 22, via the gantry 13, to enable the molecular imaging system 10 to accommodate a range of standing patients and/or sitting and/or reclining patients. Moving the gamma cameras 20 and 22 in the Y-direction, via the gantry 12, facilitate moving the gamma cameras either closer together or further apart to enable the molecular imaging system 10 to accommodate different anatomies of interest having various sizes. As such, the gamma cameras 20 and 22 are each positionable along two or three linear and separate or linear and common axes. Moreover, the gamma cameras 20 and 22 and the gantry 12 are each rotatable to accommodate different imaging modes and patient anatomies.

As discussed above, the gamma cameras 20 and 22, via the mounting brackets 66 and 68, may be either manually operated or motorized to enable the respective gamma cameras 20 and 22 to each be rotated in either a clock-wise direction 70 or a counter-clockwise direction 72. As such, the gamma cameras 20 and 22 may be repositioned to perform imaging in an L-mode configuration, an H-mode configuration, or any other configuration between the L-mode and H-mode configurations. The gamma cameras 20 and 22 may be in contact or separated and may have angles from 0° (parallel, in contact on an edge and beside each other) to 90° (contacting on and edge) to 180° (i.e. facing each other and not touching) with respect to each other.

In the L-mode configuration, shown in FIG. 1A, the gamma camera 20 is substantially perpendicular to the gamma camera 22. In the H-mode configuration, shown in FIG. 6, the imaging face of the first gamma camera 20 is approximately parallel to and facing the imaging face of the second gamma camera 22. It should be realized that although only two operational modes are discussed, e.g. L-mode and H-mode, the gamma cameras 20 and 22 may be positioned in a plurality of operational positions within each of the L-mode and H-mode positions. For example, as shown in FIG. 1A, the gamma camera 20 is positioned at a right angle with respect to the gamma camera 22. As such, the imaging face of the first gamma camera 20 is disposed at an angle that is approximately 90 (right angle) degrees from the imaging face of the second gamma camera 22. In the exemplary embodiment, the molecular imaging system 10 may also be configured in the H-mode as discussed in further detail below. In all cases the precise relative position of the detectors can be known through previous calibration or mechanical, or electrical measurement or sensors, mounted on or mounted remotely from the system 10. The positions may be automatically recorded and used to present images and/or combine views, or guide biopsy with respect to features detectable in either or both detectors.

Referring again to FIG. 4A, in the exemplary embodiment the molecular imaging system 10 also includes the biopsy needle positioning device 80 (also shown in FIGS. 1A and 1B) that is coupled to the gantry 12. The biopsy needle positioning device 80 may reposition a biopsy needle 82 (shown in FIGS. 1A and 1B) to a first position in the L-mode configuration (shown in FIGS. 1A and 1B) and to a second different position in the H-mode configuration (shown in FIGS. 8A-8C and discussed in more detail below). Referring again to FIG. 4A, the biopsy needle positioning device 80 includes a mounting plate 84 and a pressure plate 86 that is coupled to the mounting plate 84. In the exemplary embodiment, the mounting plate 84 is substantially perpendicular to the pressure plate 86. The mounting plate 84 includes a plurality of channels 88 that enable the biopsy needle 82 to move in the X-direction 74 and the Y-direction 76. Moreover, the biopsy needle 82 is also repositionable along the Z-axis. For example, the biopsy needle 82 may be moved along the Z-axis closer to or further from the gantry 12 to enable larger and smaller anatomies of interest to be biopsied.

The biopsy needle positioning device 80 is also movable along an arcuate path 90. For example, during an L-mode imaging procedure, the biopsy needle positioning device 80 is movable along the arcuate path 90 to enable the biopsy needle 82 to be positioned at an approximately 0 degrees wherein the biopsy needle 82 is positioned at a centerline between the first and second gamma cameras 20 and 22. Additionally, the biopsy needle positioning device 80 is movable along the arcuate path 90 to enable the biopsy needle 82 to be positioned at a approximately 45 degrees from the centerline 92 shown in FIG. 1A, e.g. the biopsy needle is approximately parallel to either the gamma camera 20 or the gamma camera 22 when the molecular imaging system 10 is operated in the L-mode configuration. Any other line of approach to biopsy a lesion within the breast volume is also possible with computer positioning computation and guidance or control or visualization of the entry path superimposed on the gamma camera images of the breast and the target tissue As discussed above, and shown in FIG. 4A, the biopsy needle positioning device 80 also includes the penetrable pressure plate 86. In the L-mode configuration, the pressure plate 86 and the gamma cameras 20 and 22 together form a substantially triangular anatomy capture region 87 (shown in FIGS. 1A and 1B). The anatomy capture region 87 is selectively sized to receive the anatomy of interest 24 therein. For example, the size of the anatomy capture region 87 may be increased to facilitate imaging a larger anatomy of interest by repositioning the gamma cameras 20 and 22 and the pressure plate 86 to form a larger triangular anatomy capture region 87. Moreover, to facilitate imaging a small anatomy of interest 24, the gamma cameras 20 and 22 and the pressure plate 86 may be repositioned to form a smaller triangular anatomy capture region 87. The pressure plate 86 may also be curved and the anatomy capture region accordingly different. As well the plate may be a constructed from foam or other tensile or stiff material to accomplish the same function.

Referring again to FIG. 4B, the pressure plate 86 includes a plurality of penetrations, pores, virtual openings as between the weave of a fabric or openings 96. In the exemplary embodiment, the openings 96 are arranged in rows along the Y-axis and columns along the Z-axis. Each opening 96 has a diameter that is sized to enable at least a portion the biopsy needle 82 to be inserted therethrough. In the exemplary embodiment, the pressure plate 86 is deformable to enable anatomies of interest having different sizes to be captured as is discussed in more detail below. In the exemplary embodiment, the deformable immobilizing pressure plate 86 is positioned between the first and second gamma cameras 20 and 22 to secure the anatomy of interest 24 in a substantially fixed or immobilized position during the imaging procedure.

Figure 5A:
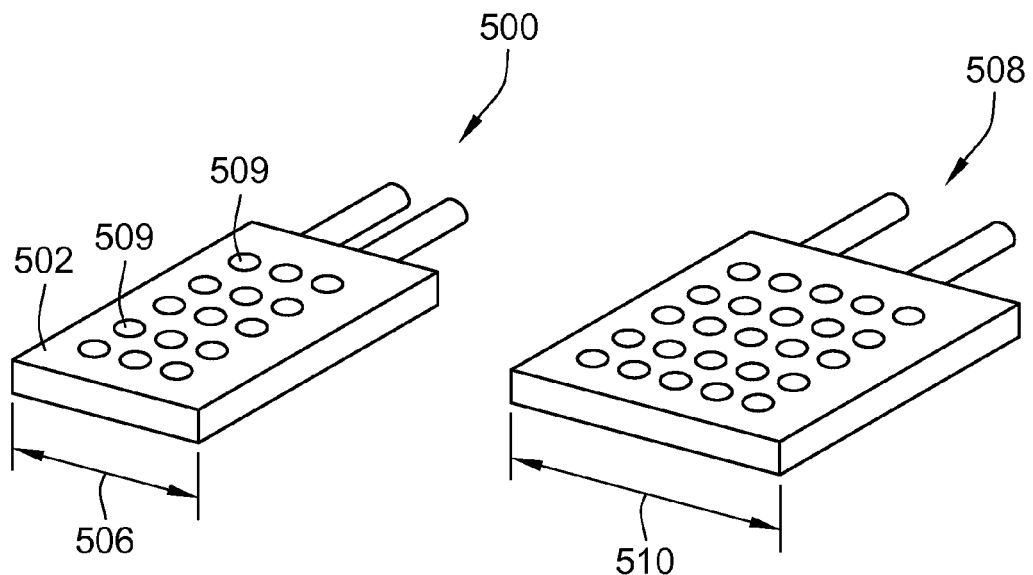
FIG. 5A is a front perspective view of an exemplary pressure plate that may be used with the imaging systems described herein in accordance with an embodiment of the present invention.

FIGS. 5A-5E illustrate several embodiments of exemplary pressure plates that may be used in lieu of pressure plate 86. For example, FIG. 5A is a front perspective view of an exemplary pressure plate 500 that may be used with the imaging systems described herein. In the exemplary embodiment, the pressure plate 500 is a removable and replaceable pressure plate 500 that has a substantially planar surface 502. The pressure plate 500 also includes a plurality of openings 504 that are sized to receive the biopsy needle 82 therethrough. The pressure plate 500 also has a width 506 that is selected to form a smaller anatomy capture region to enable a less dense breast to be imaged. Moreover, to facilitate imaging a denser or larger anatomy of interest 24, a second replaceable pressure plate 508 may be utilized. The second pressure plate 508 is substantially similar to the pressure plate 500, however a width 510 of the second pressure plate 508 is greater than the width 506 of the pressure plate 500 to enable a denser breast to be imaged. Specifically, the wider pressure plate 508 forms a larger capture region to enable a larger or denser breast to be imaged. It should be realized that although only two replaceable pressure plates are illustrated, that a variety of pressure plates having various widths may be utilized to image a variety of breasts of varying sizes and density. The pressure plates 500 and 508 are coupled to the imaging system in the same manner as discussed above regarding pressure plate 86.

Figure 5B:
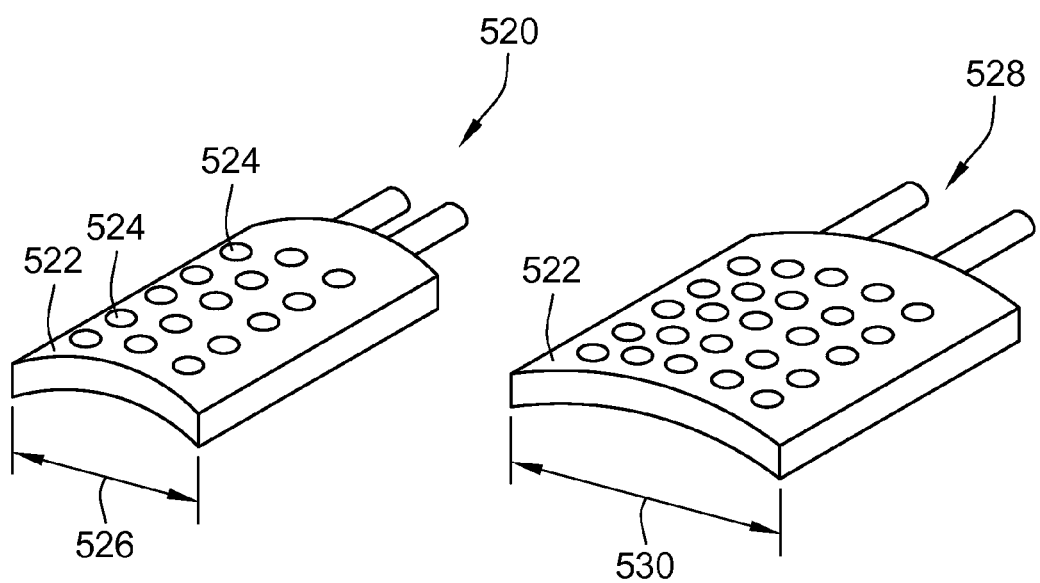
FIG. 5B is a front perspective view of another exemplary pressure plate that may be used with the imaging systems described herein.

FIG. 5B is a front perspective view of another exemplary pressure plate 520 that may be used with the imaging systems described herein. In the exemplary embodiment, the pressure plate 520 is a removable and replaceable pressure plate that has a substantially curved surface 522. The pressure plate 520 also includes a plurality of openings 524 that are sized to receive the biopsy needle 82 therethrough. The pressure plate 502 also has a width 526 that is selected to form a smaller anatomy capture region to enable a less dense breast to be imaged. Moreover, to facilitate imaging a denser or larger anatomy of interest 24, a second replaceable pressure plate 528 having a curved surface 522 may be utilized. The second pressure plate 528 is substantially similar to the pressure plate 520, however a width 530 of the second pressure plate 528 is greater than the width 526 of the pressure plate 520 to enable a denser breast to be imaged. Specifically, the wider pressure plate 528 forms a larger capture region to enable a larger or denser breast to be imaged. It should be realized that although only two replaceable pressure plates are illustrated, that a variety of pressure plates having various widths may be utilized to image a variety of breasts of varying sizes and density. The pressure plates 520 and 528 are coupled to the imaging system in the same manner as discussed above regarding pressure plate 86.

Figure 5C:
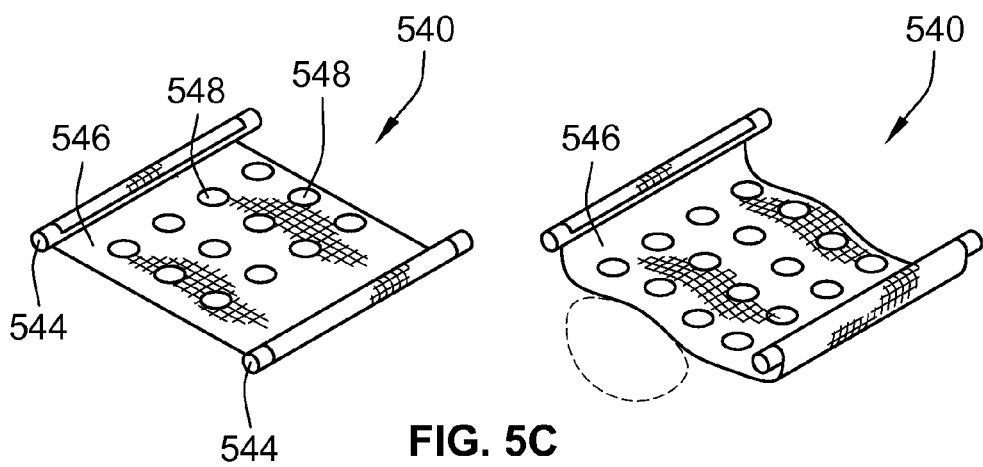
FIG. 5C is a front perspective view of another exemplary pressure plate that may be used with the imaging systems described herein.

FIG. 5C is a front perspective view of another exemplary pressure plate 540 that may be used with the imaging systems described herein. In the exemplary embodiment, the pressure plate 540 is a removable and replaceable pressure plate that has a flexible portion 542. More specifically, the pressure plate 540 includes two substantially rigid side member 544 and a flexible portion 546 that is coupled between and to the rigid side members 544. The pressure plate 540 also includes a plurality of openings 548 that are sized to receive the biopsy needle 82 therethrough. The pressure plate 540 also has a width 550 that is selected to enable any size breast to be imaged. As shown in the FIG. 5C, during operation, the flexible portion 546 deforms or flexes when placed in contact with a breast to be imaged. The flexing or deforming movement enables the pressure plate to immobilize any size breast during the imaging procedure. The pressure plates 540 is coupled to the imaging system in the same manner as discussed above regarding pressure plate 86.

Figure 5D:
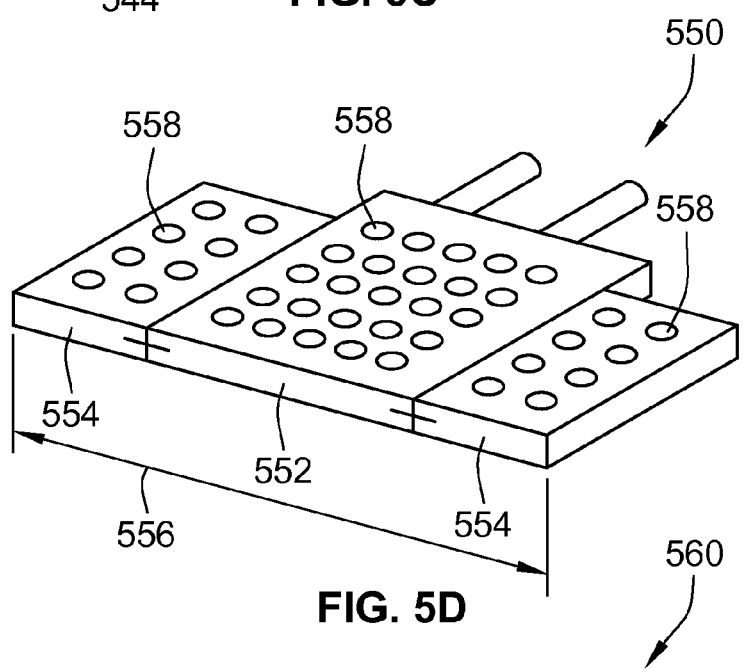
FIG. 5D is a front perspective view of another exemplary pressure plate that may be used with the imaging systems described herein.

FIG. 5D is a front perspective view of another exemplary pressure plate 550 that may be used with the imaging systems described herein. In the exemplary embodiment, the pressure plate 550 is a removable and replaceable pressure plate. The pressure plate 550 includes a main body portion 552 and at least two extensions 554 that are coupled to the body portion 552. As shown in FIG. 5D each extension is mounted to a side of the body portion 552 to either increase or decrease a width 556 of the overall pressure plate 550. More specifically, the image a smaller or less dense breast, the pressure plate 550 may be utilized without the extensions 554. However, to image a larger or denser breast, the extensions 554 may be coupled to the sides of the body portion 552 thereby increasing the overall width of the pressure plate 550 to enable larger breasts to be imaged. It should be realized that a variety of extensions, each having a predetermined width may be utilized to define a pressure plate having a predetermined width based on the size of the breast to be imaged. The body portion 552 and the extensions 554 each include a plurality of openings 558 that are sized to receive the biopsy needle 82 therethrough. Moreover, the openings 558 in the extensions are substantially aligned with the openings 558 in the body portion. The pressure plate 550 is coupled to the imaging system in the same manner as discussed above regarding pressure plate 86.

Figure 5E:
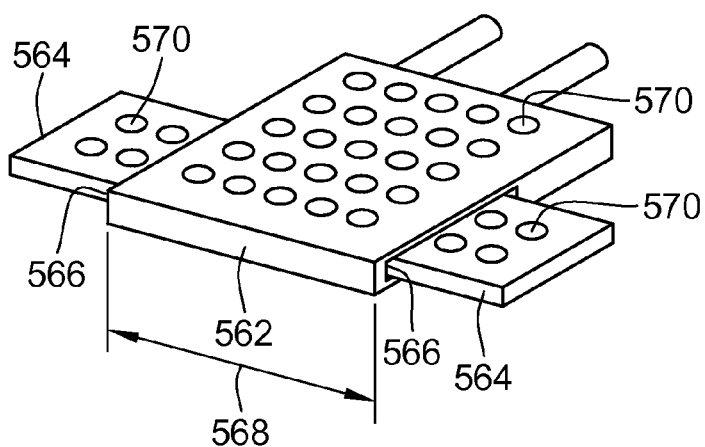
FIG. 5E is a front perspective view of another exemplary pressure plate that may be used with the imaging systems described herein.

FIG. 5E is a front perspective view of another exemplary pressure plate 560 that may be used with the imaging systems described herein. In the exemplary embodiment, the pressure plate 560 is a removable and replaceable pressure plate. The pressure plate 560 includes a main body portion 562 and at least two telescopic extensions 564 that are coupled to the body portion 562. As shown in FIG. 5E each extension extends from a recess 566 that is formed in a respective side of the body portion 562. During operation, to image a smaller or less dense breast, the extensions 564 may be fully retracted into the body portion 562. However, to image a larger or denser breast, the extensions 564 are at least partially extended from the body portion 562. More specifically, a width 568 of the pressure plate 560 may be adjusted by either extending or retracting the extensions 564. In this manner, a larger variety of breasts of different sizes may be imaged without removing or replacing the pressure plate. It should be realized that a variety of extensions 564, each having a predetermined width may be utilized to define a pressure plate 560 having a predetermined width based on the size of the breast to be imaged. The body portion 562 and the extensions 564 each include a plurality of openings 570 that are sized to receive the biopsy needle 82 therethrough. Moreover, the openings 570 in the extensions are substantially aligned with the openings 570 in the body portion. The pressure plate 560 is coupled to the imaging system in the same manner as discussed above regarding pressure plate 86.

During the imaging operation, the molecular imaging system 10 is configured to enable the anatomy of interest 24 to be imaged to detect lesions, tumors, or other medical information. In the exemplary embodiment, the anatomy of interest 24 is a breast of a human patient. Moreover, in the exemplary embodiment, the patient is in a sitting position upon a chair and the breast is disposed between, and resting upon, the gamma cameras 20 and 22. During operation, a radiopharmaceutical that concentrates in a predetermined region of the breast is injected into a patient. The patient is then seated at the molecular imaging system 10 such that the patient's breast is positioned between the pair of gamma cameras 20 and 22. As discussed above, the molecular imaging system may be configured in an L-mode configuration, an H-mode configuration, or any other configuration between the L-mode and H-mode configurations. The gamma cameras 20 and 22 are then adjusted to capture the breast and immobilize it for the duration of the scan. In H mode CC view the breast is captured from top and bottom with the camera surfaces. In H mode ML or MLO the assistance of the retaining plate may assist to keep the tissue within the field of view from below. In L mode the biopsy plate or equivalent may be used to capture with immobilization.

In the exemplary embodiment, the tissue capture is accomplished with a immobilizing force that is less than a compression force applied to the breast during a conventional mammography imaging procedure. For example, as discussed above, conventional mammographic imaging systems apply a compression force to the breast to flatten the breast, spreading out the tissue and separating the structural features, and thereby improving image quality. The conventional mammographic imaging system may apply a sufficient compression force to the breast to cause the patient discomfort. Whereas, during operation of the molecular breast imaging system 10 an immobilizing force is applied to the breast to ensure that the breast is stationary during the imaging process. Moreover, the immobilizing force is selected to ensure that the breast is disposed on the gamma cameras 20 and 22 and the tissue is entirely within the capture region. In the exemplary embodiment, the immobilizing force selected is sufficient to maintain the breast in a stationary position against the gamma cameras 20 and 22. Moreover, the immobilizing force is less than the compression force applied by a conventional imaging system to perform mammographic imaging. Moreover tissue spreading to separate structural features is not required for the molecular breast imaging system 10 since the said structural features are not present in molecular breast imaging. Moreover, a compression force would often result in tissue being forced out of the field of view and failure of the molecular breast imaging system to detect disease. Therefore, using an immobilizing force facilitates providing a more comfortable examination and while still providing image quality sufficient to significantly enhance the performance of tumor and lesion detection compared to conventional mammography.

After the immobilizing force is applied to the anatomy of interest 24, the gamma cameras 20 and 22 are activated to generate an image of the anatomy of interest. In the exemplary embodiment, gamma camera 20 produces a first medical image and gamma camera 22 produces a different second medical image. The medical images may be viewed one at a time, or side-by-side on the display 34. In another embodiment, the processor 36 includes instructions to combine the images. More specifically, the processor 36 may include instructions to register the first image and the second image to generate a combined image. In one embodiment, the combined image is a two-dimensional image of the anatomy of interest 24. Optionally, the combined image is a three-dimensional image of the anatomy of interest. Moreover, in the L-mode configuration, the molecular imaging system 10 generates two views of the anatomy of interest that are acquired from two non-colinear projection angles to generate a projection dataset of the volume of anatomy of interest 24. The two views represent the projection dataset. The collected projection dataset is then utilized to generate a three-dimensional dataset, representative of the three-dimensional representation of imaged anatomy of interest 24. In another embodiment, the projection dataset is deconvolved using the data acquired from the two gamma cameras 20 and 22 to ascertain a true planar projected size, position, and strength of the lesion or tumor without the distorting effects of the detector resolution function. Deconvolution may for example be achieved by refining an initial guess based on iterative forward projection using the collimator response function to obtain a test projection dataset and back projection of the difference between the test projection dataset and the measured projection dataset. Deconvolution may also be achieved by comparing the 6 values of diameter and position measured by the 2 cameras to a stored lookup table of lesion size, radioactivity strength, and position. Alternatively partial lookup and partial iterative can be combined to ascertain the lesion size, radioactivity strength, and position. The improved lesion image obtained by removal of the collimator response function is used to improve decisions of whether an observed imaging feature is a statistically significant region of tracer uptake as opposed to a background noise fluctuation, as well as to more accurately target the center of the lesion with the biopsy needle. The information of the absolute lesion uptake ratio (compared to normal tissue) may also prove to be usefully correlated to the tissue pathology in the future.

Figure 6A:
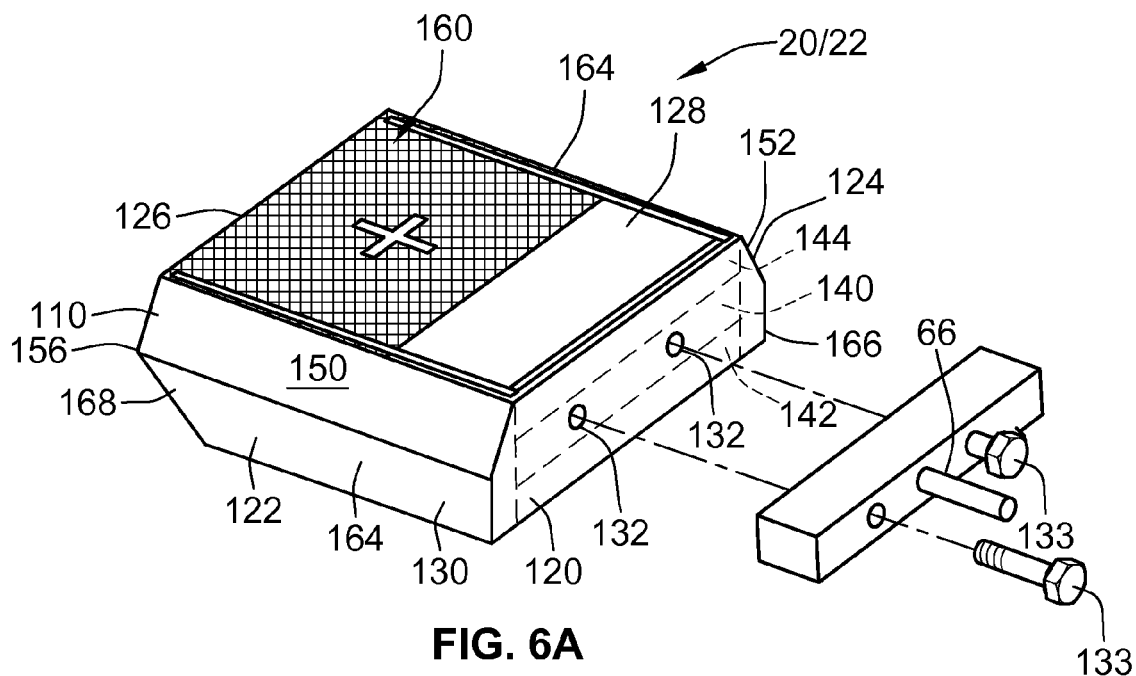
FIG. 6A is a back perspective view of the gamma camera shown in FIGS. 1 and 2 in accordance with an embodiment of the present invention.
Figure 6B:
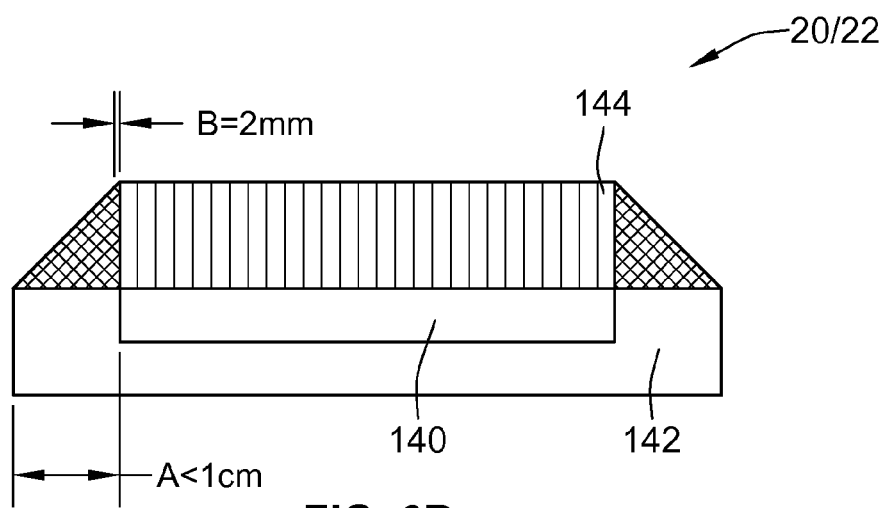
FIG. 6B is a front view of the gamma camera shown in FIG. 6A.

FIG. 6A is a perspective view of the gamma camera 20 shown in FIGS. 1-1A and 1B. FIG. 6B is a front view of the gamma camera 20 shown in FIG. 6A. In the exemplary embodiment, gamma camera 20 is substantially similar to the gamma camera 22. As such, the gamma camera 20 and the gamma camera 22 include an external housing 110. In the exemplary embodiment, the housing 110 is substantially square or rectangular and includes a first side 120, a second side 122 that is substantially perpendicular to the first side 120, a third side 124 that is approximately parallel to the second side 122, and a fourth side 126 that is substantially parallel to the first side 120. Moreover, the housing 110 includes a first surface 128 and an opposing second surface 130. In the exemplary embodiment, the first surface 128 is a gamma emission detecting surface and is referred to herein as the detecting face 128. The first side 120 is configured to enable the first gamma camera 20 to be reproducibly mounted to the gantry 12 via the mounting bracket 66 as shown in FIG. 2 and discussed above. Additionally, the mounting bracket 68 enables the first side 120 of the second gamma camera 22 to be reproducibly mounted to the gantry 12. Side 126 may include a chamfer if the structure of the camera is larger in the plane of 156 than the parallel plane in the Field of view 160.

Referring again to FIG. 6A, in one embodiment, the first side 120 includes at least two openings 132 that are adapted to receive a bolt 133 at least partially therein. The combination of the bolts 133 and the openings 132 enable the mounting brackets 66 and 68 to be coupled to the gamma camera 20 and gamma camera 22, respectively, and thus also be coupled reproducibly to the gantry 12. Optionally, other mounting guide mechanisms such as pins or edges and latches or interlocks may be used to reproducably mount the detectors.

The gamma camera 20 also includes a Cadmium Zinc Telluride (CZT) detector array 140, an electronics device 142, and a collimator 144. As shown in FIG. 5, the gamma camera 22 also includes a Cadmium Zinc Telluride (CZT) detector array 141, an electronics device 143, and a collimator 145. More specifically, the detector arrays 104 and 141 may be fabricated of a compact Cadmium Zinc Telluride (CZT) semiconductor, or alternative compact detector such as from CdTe or HgI or CsI or others. A photoconduction process within the CZT semiconductor generates electron-hole pairs in an interaction with gamma photons. The electrons and/or holes move toward respective electrodes of the electronics device 142/143 generating an output electrical signal comprising photon count, position, and energy data.

During operation, the patient is injected with a radiopharmaceutical that concentrates in known regions of the anatomy of interest and emits emission gamma rays. Subsequently, the anatomy of interest, in this case, the breast, 24 is positioned between the gamma cameras 20 and 22 as discussed above. The gamma rays emitted from the anatomy of interest 24, are collimated by the collimators 144/145 to produce an image. The collimated gamma rays are then detected by the respective CZT detector arrays 140/141. The output from the CZT detector arrays 140/141 are input to the respective electronics devices 142/143 to be output as an electrical signal comprising photon count, position, and energy data. The outputs from the electronics devices 142/143 are used to reconstruct or generate an image of the anatomy of interest 24.

Figure 7:
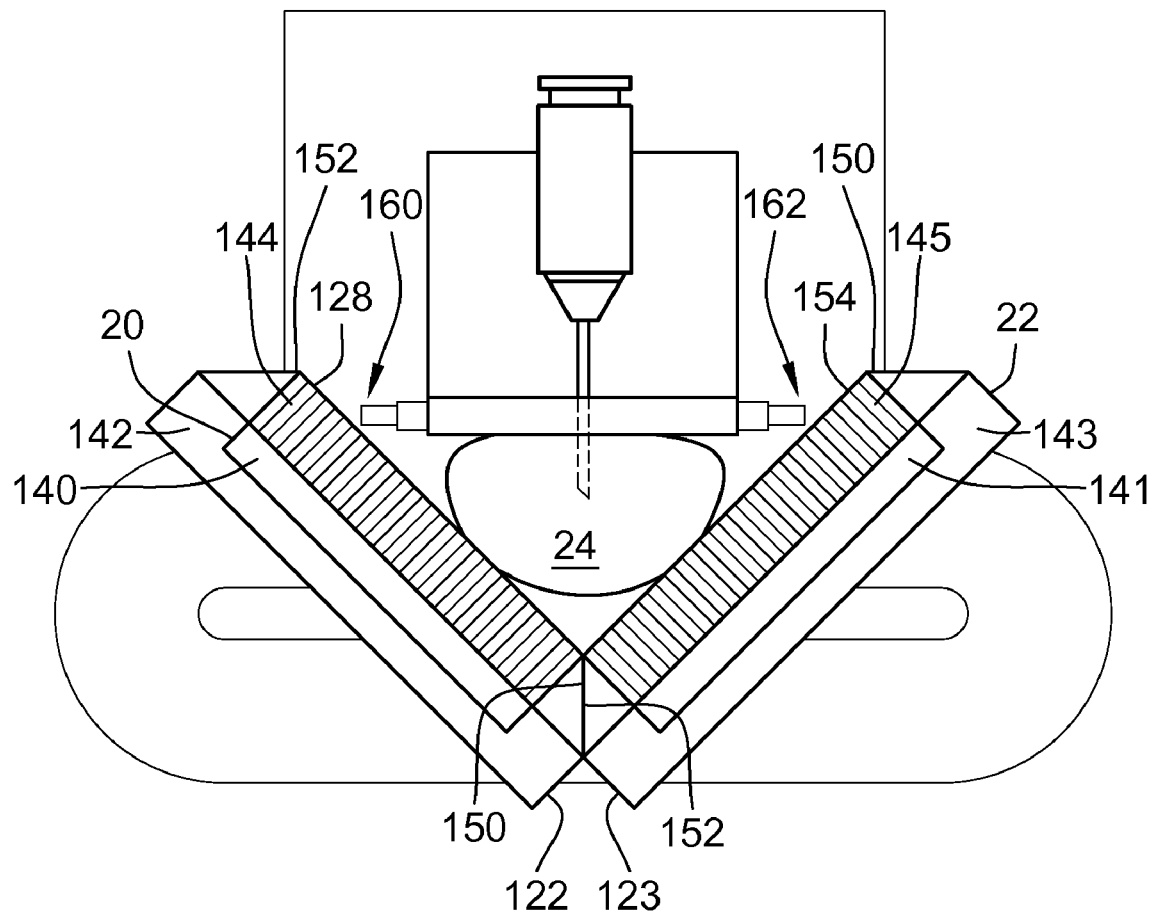
FIG. 7 is a perspective view of a portion of the imaging system shown in FIGS. 1A and 1B in a first operational configuration.

Referring to FIG. 7, as discussed above in the L-mode configuration it is desirable to position the gamma cameras 20 and 22 as close together as possible to improve image quality, and to position the gamma cameras 20 and 22 as close to the patient as possible to facilitate minimizing the loss of resolution. For example, conventional detectors include a housing that limits the distance the detectors may approach during the imaging process. Specifically the field of view of conventional detectors is typically separated by a distance that is at least 5 millimeters and may be as high as 7 cm. As such, conventional detectors may be unable to identify lesions or tumors that are located in the gap defined between the conventional detectors. Furthermore they may be unable to see with both cameras a lesion that is located on the surface of the anatomy of interest and therefore close to one camera and out of the field of view of the other camera.

In the exemplary embodiment, to improve image quality and to facilitate eliminating the gap between conventional detectors, at least a portion the housings of gamma cameras 20 and 22 are chamfered to enable the gamma camera 20 to contact the gamma camera 22 during the imaging procedure and for the close region of each camera to be seen by the other camera as well. More specifically, referring again to FIG. 6A, each of gamma cameras 20 and 22 include at least two chamfered or tapered edge 150 and 152, respectively, that enables the gamma camera 20 to contact the gamma camera 22, when the gamma cameras 20 and 22 are arranged in the L-mode configuration. More specifically, in the exemplary embodiment, one chamfered edge 150 is formed on the second side 122 of the gamma camera 20 and a second chamfered edge 152 is formed in the third side 124 of the gamma camera 20. The chamfered edges 150/152 each extend along the length of the sides 122/124 and also extend from a horizontal line 156 to the detecting face 128 of the gamma camera 20. In the exemplary embodiment, the chamfered edges 150/152 are disposed at the mating edges of each of the gamma cameras such that each gamma camera can view tissue within the first mm of the surface of the opposing gamma camera. The line 156 is best formed from the mating surface of the collimator to the respective detector. The collimator holes are registered to the CZT detector pixels.

In the exemplary embodiment, the chamfered edges 150/152 are each chamfered at an angle of approximately 45 degrees from the detecting face 128 to the horizontal line 156. As such, since both gamma cameras 20 and 22 include the chamfered edges 150 and 152, when the gamma cameras 20 and 22 are positioned in the L-mode, the detecting face 128 of the first gamma camera 20 is at an approximate 45 degree angle from the detecting face 128 of the second gamma camera 22 as shown in FIG. 7. Moreover, when the first gamma camera 20 and the second gamma camera 22 are in the L-mode configuration, a field-of-view 160 of the first gamma camera 20 extends to a field-of-view 162 of the second gamma camera 22. The field of views 160 and 162 are each illustrated by the cross-hatched areas in the various figures. In the exemplary embodiment, the field-of-view 160 is approximately touching without overlapping the field-of-view 162 in this exemplary embodiment. In the exemplary embodiment, the fields-of-view 160 and 162 are separated by a distance that is less than 5 millimeters to enable lesions and/or tumors having a diameter that is less than approximately 5 millimeters to be imaged in the L-mode configuration as shown in FIG. 7.

Referring again to FIG. 4, each of gamma cameras 20 and 22 also include at least a third surface 164 and a fourth surface 166. More specifically, the second and third sides 122 and 124 are approximately perpendicular to the bottom and top surfaces. Chamfering both sides of the detector as discussed above, enables each gamma camera 20 and 22 to be mounted in either the left-hand or right-hand position on the gantry 12. More specifically, chamfering both 122 and 124 facilitates fabricating gamma camera 20 substantially the same as gamma camera 22 and therefore facilitates repair and replacement and production of gamma cameras.

To improve patient comfort, each of gamma cameras 20 and 22 may also include a chamfered edge 168 shown in FIG. 6A. In the exemplary embodiment, each gamma camera 20 and 22 includes the chamfered edge 168 that is formed on the fourth side 126 of the gamma camera. As shown in FIG. 6A, the front chamfered edge 168 extends from the horizontal centerline 156 to the second surface 130. In operation, the chamfered edge 168 reduces patient discomfort by eliminating sharp edges that may contact a patient during the imaging procedure. As such, the chamfered edges 168 enable a patient to be positioned contacting the gamma cameras 20 and 22 without the patient being jabbed or otherwise discomforted by relatively sharp edges as is known in conventional gamma cameras.

Figure 8A:
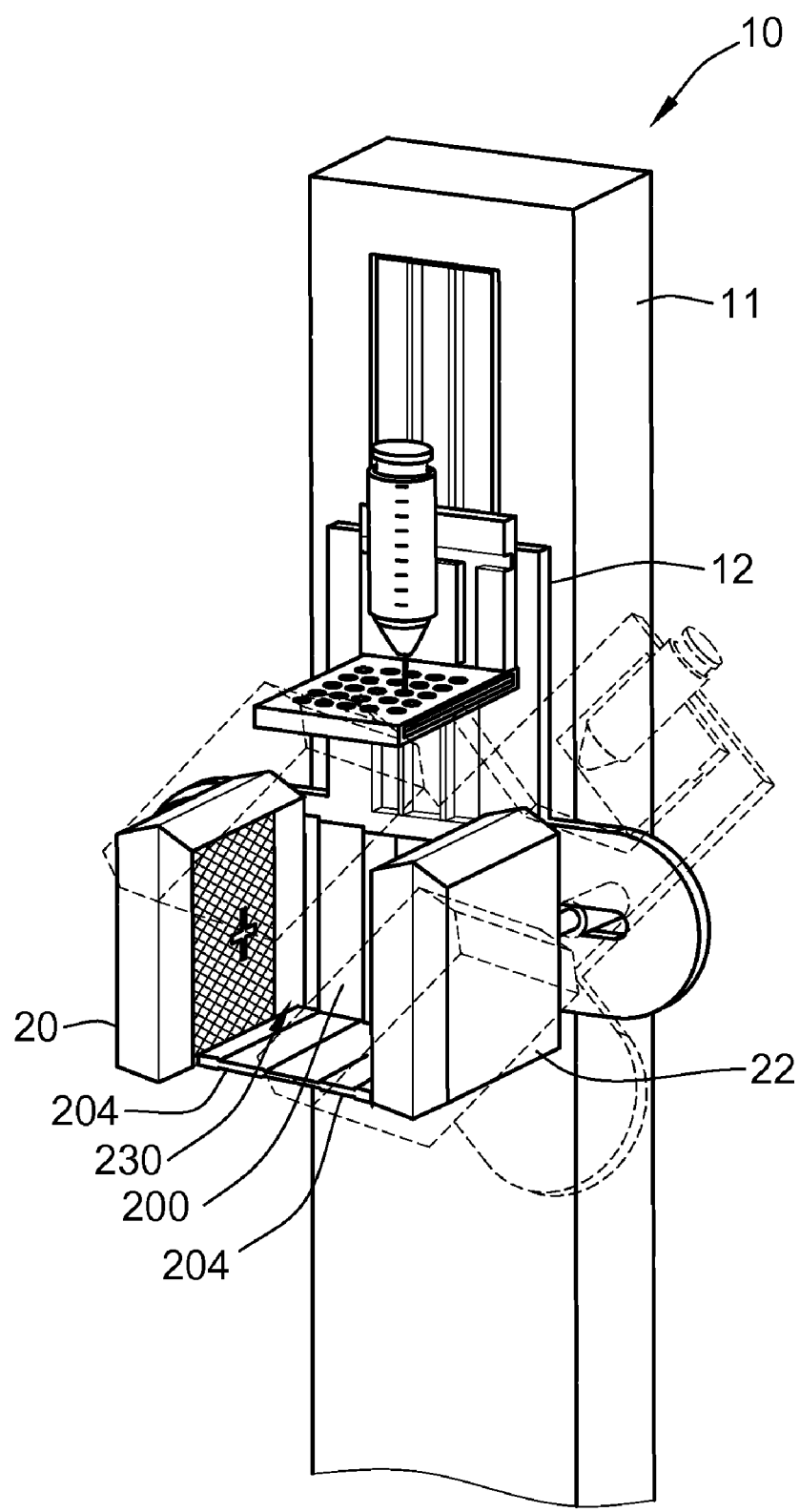
FIG. 8A is a front perspective view of the imaging system shown in FIGS. 1A and 1B in another exemplary operational position in accordance with an embodiment of the present invention.

FIGS. 8A-8E are perspective views of the molecular imaging system 10 configured in various H-mode configurations wherein the gamma camera 20 is approximately parallel to the gamma camera 22. For example, as shown in FIG. 8A, the gamma cameras 20 and 22 may be rotated to support mediolateral and medial-lateral oblique imaging wherein the gamma cameras 20 and 22 are disposed at the sides or angle to the anatomy of interest 24. Additionally, in the H-mode, the gamma cameras 20 and 22 may be rotated to support craniocaudal imaging wherein the gamma camera 20 is disposed at the top of the anatomy of interest 24 and the gamma camera 22 is disposed at the bottom of the anatomy of interest 24.

Figure 8B:
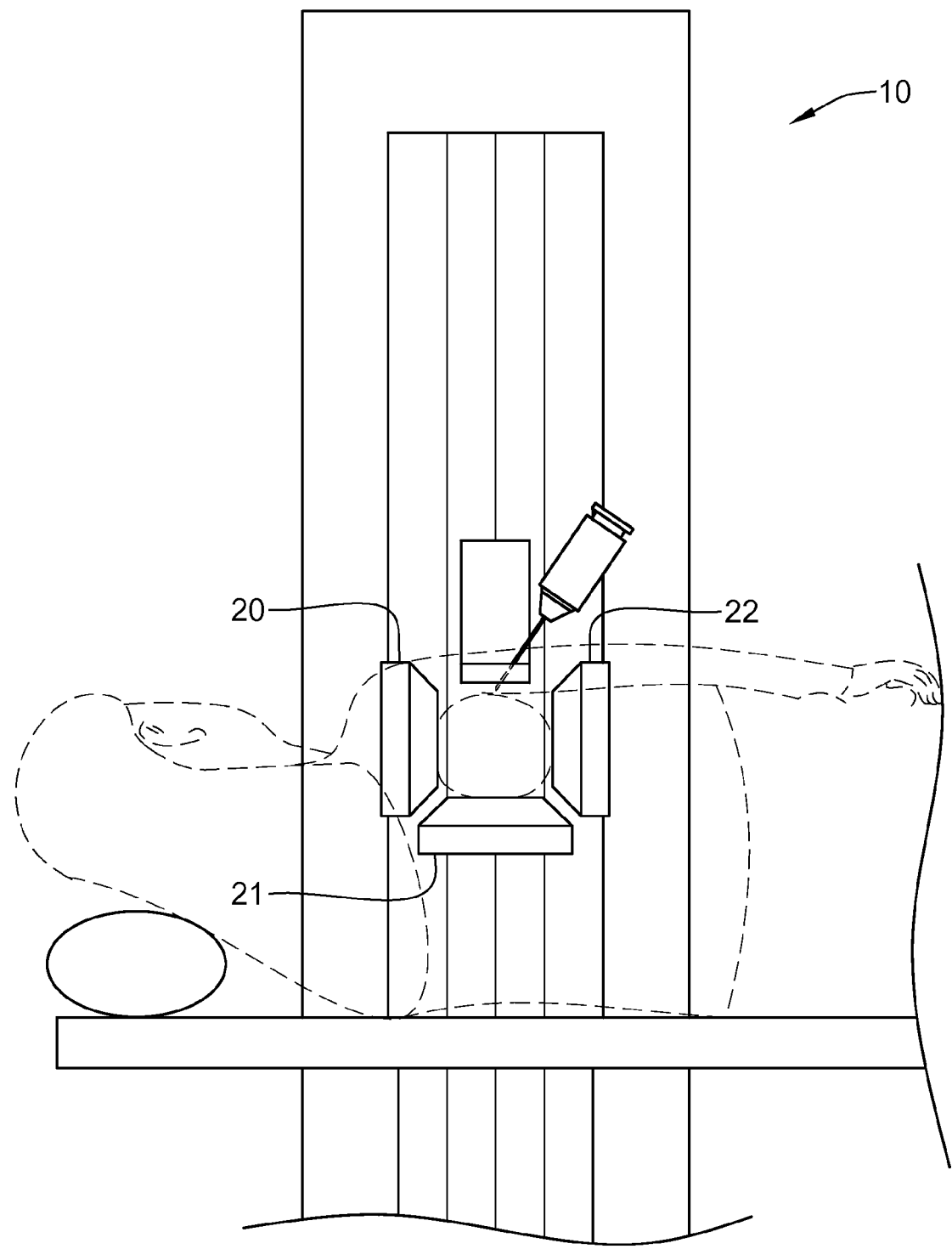
FIG. 8B is a front view of the imaging system shown in FIGS. 1A and 1B in another exemplary operational position.

As shown in FIG. 8B, the gamma cameras 20 and 22 may be rotated to image a patient in a reclined position, for example, a patient lying on a table. In all modes described herein, the gamma cameras 20 and 22 and the pressure plate are movable in an up and down configuration to support imaging patients either sitting, standing or reclining on a table. Moreover, as shown in FIG. 8B, the imaging system may include a third gamma camera 20. In the exemplary embodiment, the third gamma camera 21 is configured to perform imaging and to also to maintain the breast within the imaging field of view of the first and second gamma cameras 20 and 22.

Figure 8C:
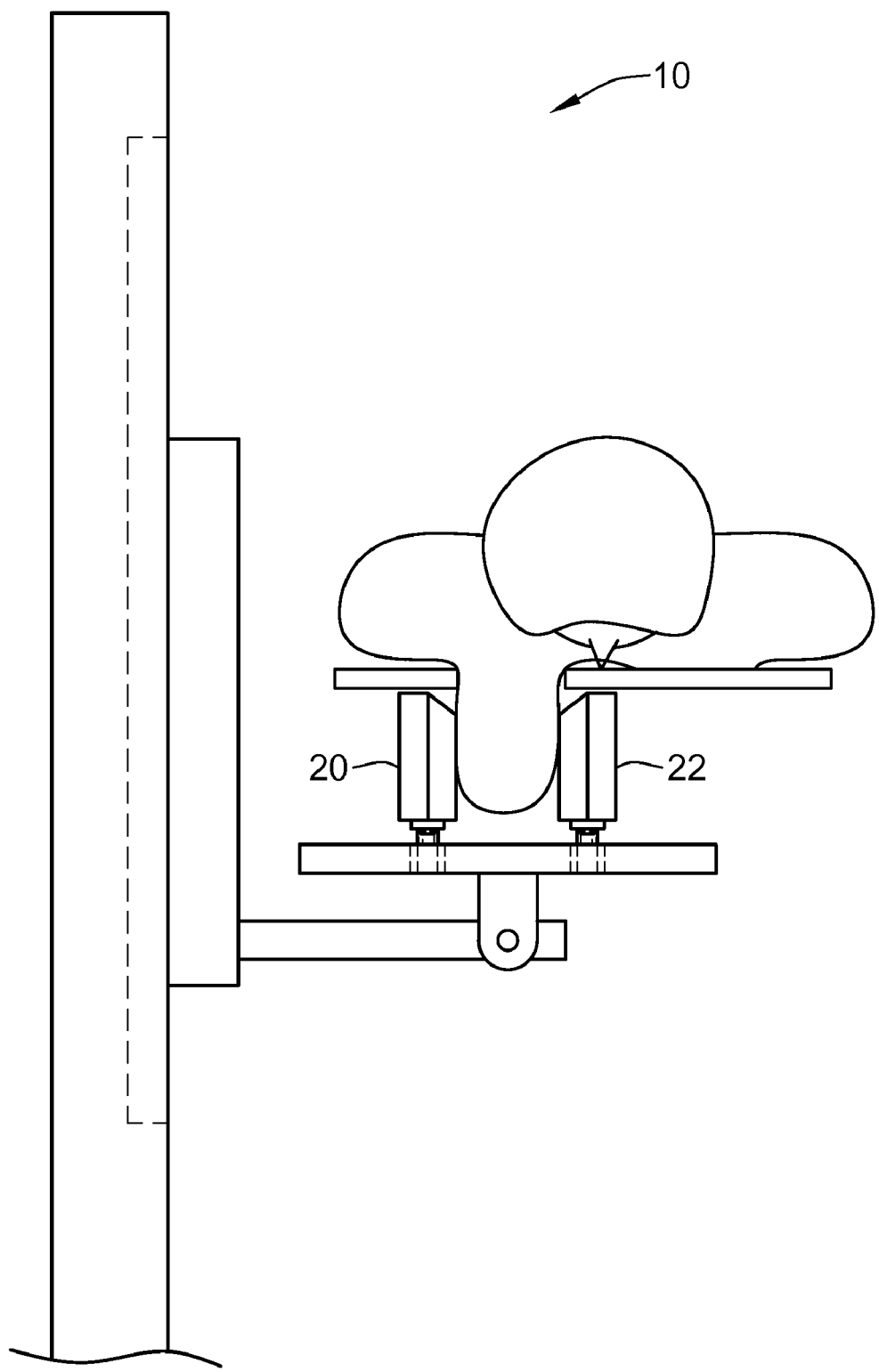
FIG. 8C is a side view of the imaging system shown in FIGS. 1A and 1B in another exemplary operational position.
Figure 8D:
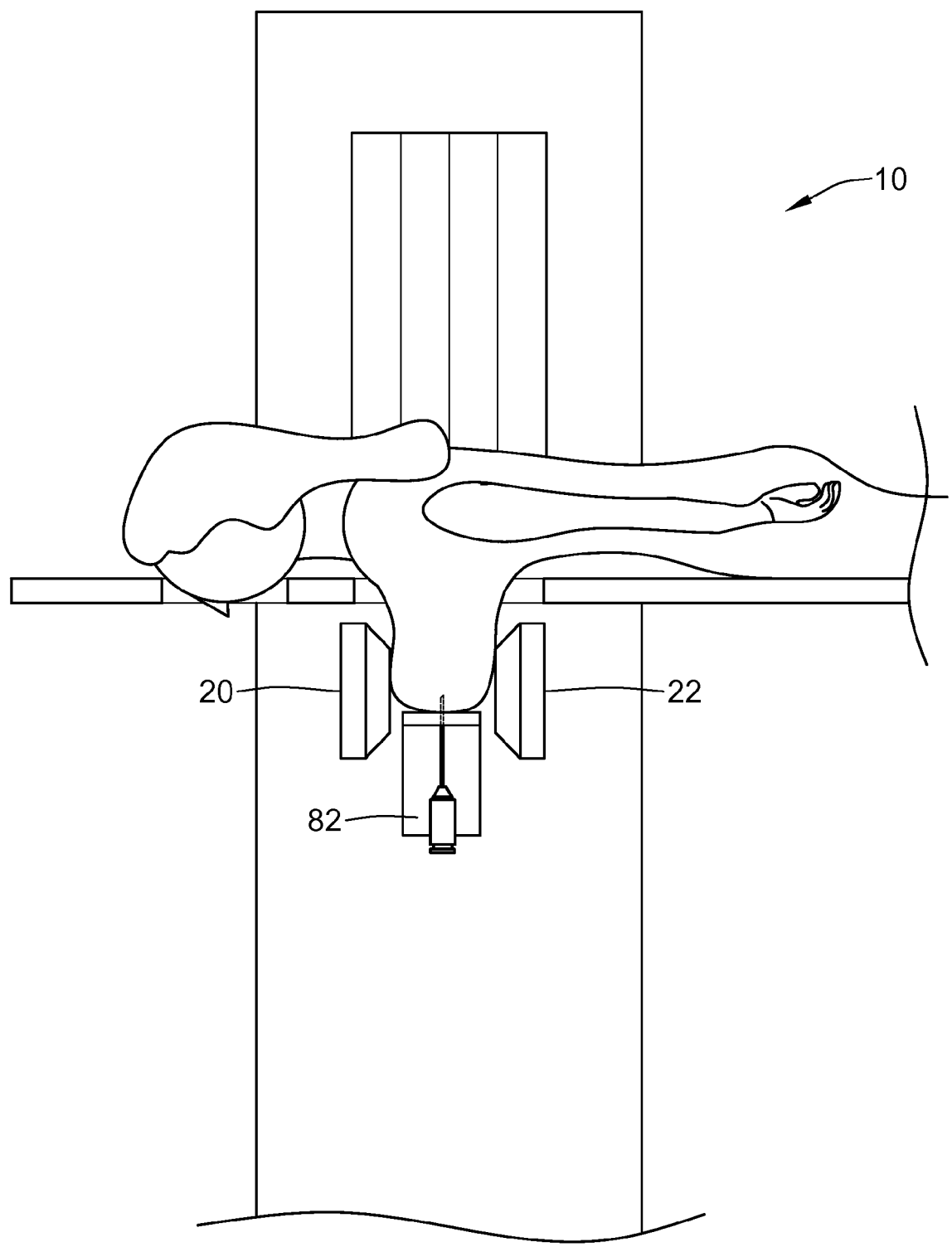
FIG. 8D is a front view of the imaging system shown in FIGS. 1A and 1B in another exemplary operational position.
Figure 8E:
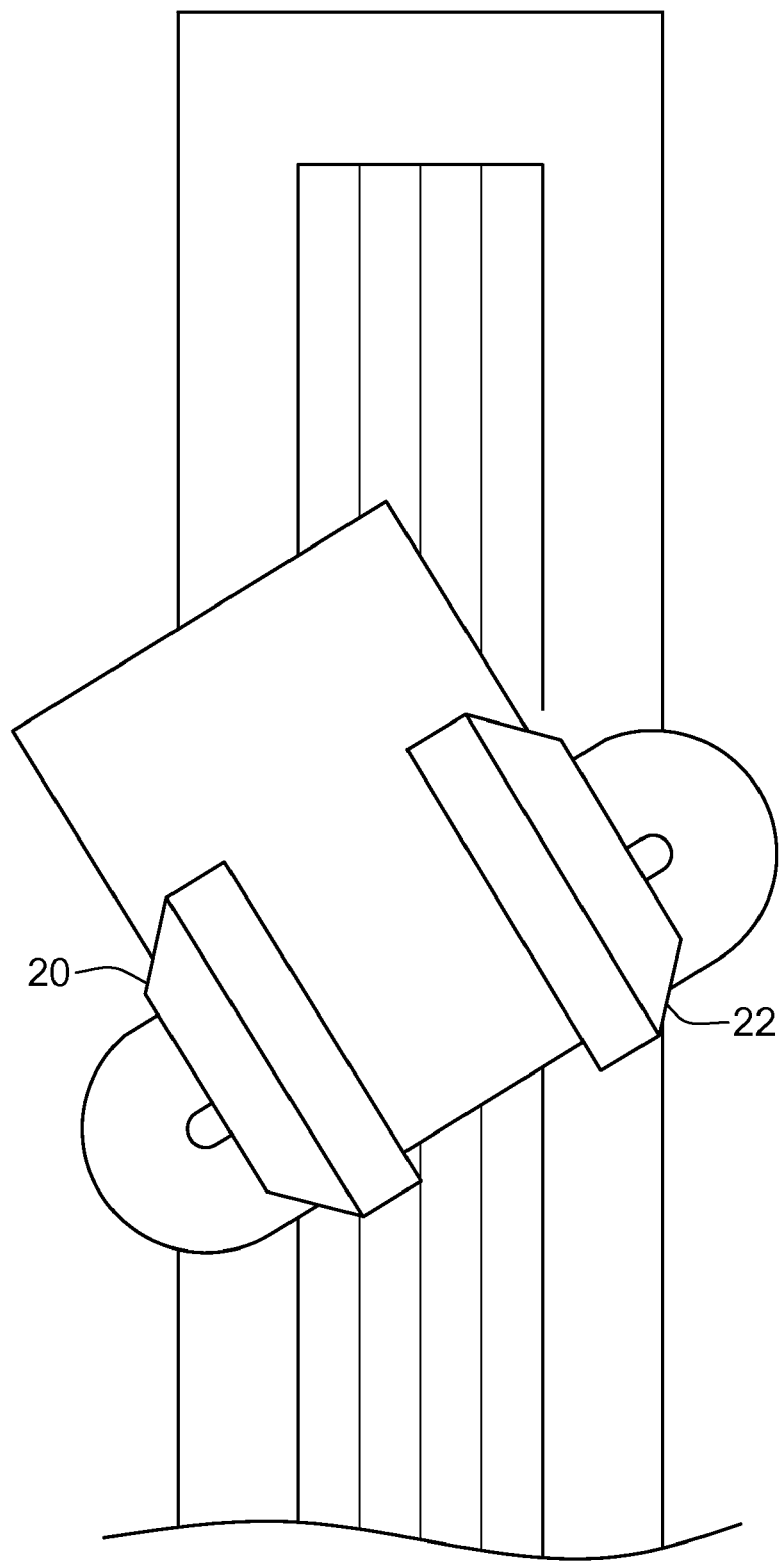
FIG. 8E is a side view of the imaging system shown in FIGS. 1A and 1B in another exemplary operational position.

As shown in FIG. 8C, the gamma cameras 20 and 22 may be rotated to image a patient in a lateral view. Specifically, the patient is laying face down on an imaging table and the breast extends through an opening in the table such that the breast is disposed between the pair of gamma cameras. As shown in FIG. 8D, the biopsy needle positioning device 82 is also rotatable to perform a biopsy in this position. In the exemplary embodiment, the imaging system may be configure to support medio-lateral and medial-lateral oblique imaging wherein the gamma cameras 20 and 22 are disposed at the sides or angle to the anatomy of interest 24. Additionally, in the H-mode, the gamma cameras 20 and 22 may be rotated to support cranio-caudal imaging wherein the gamma camera 20 is disposed at the top of the anatomy of interest 24 and the gamma camera 22 is disposed at the bottom of the breast. As shown in FIG. 8E the gamma cameras 20 and 22 may be turned parallel and side by side or turned out for calibration and special anatomical positions. More specifically, the gamma cameras 20 and 22 may be arranged such that the imaging surfaces of each gamma camera are extending 180 degrees away from each other to enable a breast to be positioned on top of the gamma camera.

Figure 9A:
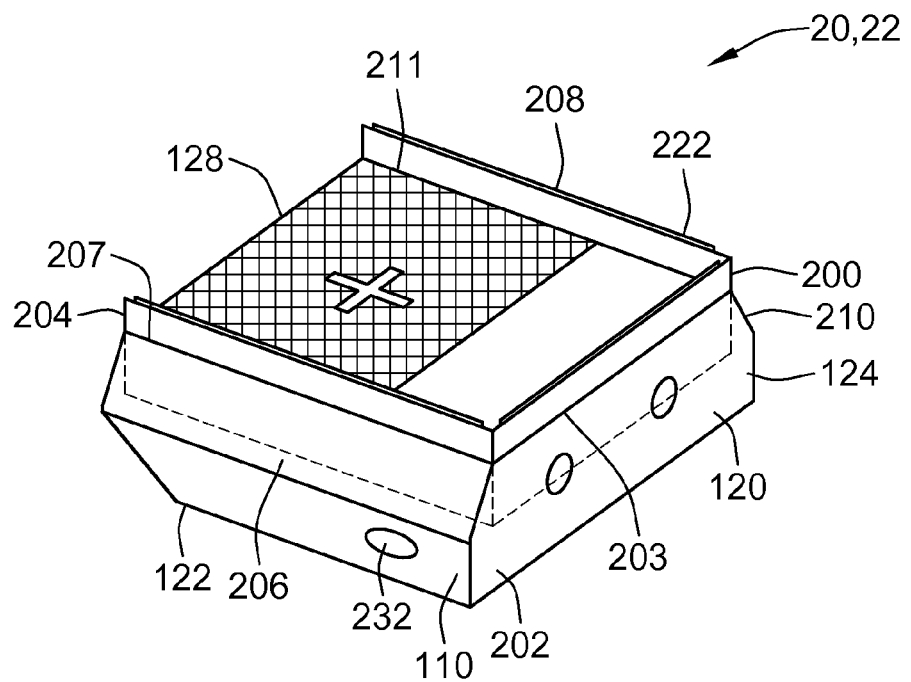
FIG. 9A is perspective view of the gamma camera shown in FIG. 8A in a first operational position.

FIG. 9A is a perspective view of the gamma camera 20 shown in FIGS. 6A and 6B and including at least one retractable retaining device or wall 200. It should be realized that although FIG. 9A describes gamma camera 20, that the retractable walls described herein may also be included in the gamma camera 22. But for ease of discussion, only gamma camera 20 is described and illustrated. As discussed above, when conventional detectors are configured for H-mode medial lateral or medial lateral oblique imaging, during imaging, gravity may cause a breast positioning error such that a portion of breast including a lesion is out of the field of view of the gamma detectors. Thus, the portion of breast outside the gamma detectors field of view is not properly imaged. As such, in the exemplary embodiment, at least one of gamma cameras 20 and/or 22 includes at least one retractable retaining device or wall to maintain the anatomy of interest 24 in a field-of-view of the first and second gamma cameras 20 and 22.

As shown in FIG. 9A, the gamma cameras 20 and/or 22 includes a first retractable wall 200 that is stored in and extends from a first recess 202 that is formed in the housing 110. In the exemplary embodiment, the gamma camera 20 also includes a second retractable wall 204 that is stored in and extends from a second recess 206 formed in the housing 110 and a third retractable wall 208 that is stored in and extends from a third recess 210 in the housing 110. The first recess 202 is defined between the inner wall of the first side 120 and the combination of the detector array 140, the electronics device 142, and the collimator 144 shown in FIG. 6A. More specifically, the housing 110 includes a space or recess that is located between the detector portions and the internal surface of the housing 110 that is sized to receive a retractable wall. In the exemplary embodiment, the first recess 202 includes an opening 203 that is formed through the detecting face 128 proximate to the first side 120, the second recess 206 includes an opening 207 that is formed through the detecting face 128 proximate to the second side 122, and the third recess 210 includes an opening 211 that is formed through the detecting face 128 proximate to the third side 124. During operation, the retractable walls are stored in the respective recesses and then extended through a respective opening in the detector face. The retaining function is also achievable using an accessory added foam or cloth retaining device.

Figure 9B:
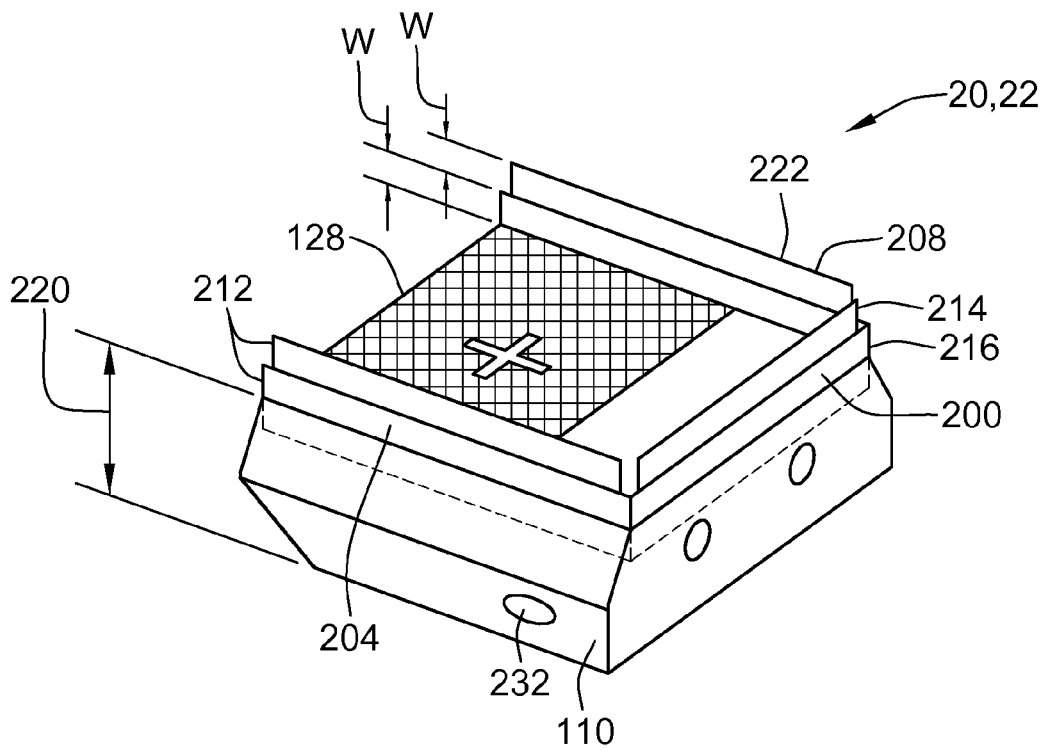
FIG. 9B is perspective view of the gamma camera shown in FIG. 9A in a second operational position.

As shown in FIG. 9B, in one embodiment, the retractable walls 200, 204, and 208 may each include a plurality of wall portions 212 that are coupled together to form the respective retractable wall. More specifically, the portions 212 are slidably coupled together such that each retractable wall may be fully retracted into the respective recess or fully extended from the respective recess. For example, in the exemplary embodiment, each retractable wall 200, 204, and 208 includes at least two portions 214 and 216 each having a width W. Thus when the retractable wall is fully retracted, each retractable wall has a width that is approximately equal to W. In the exemplary embodiment, the detector housing 110 has a width 220 that is greater than W to enable the retractable walls to be fully stored within a respective recess formed within the housing 110. When the retractable wall is fully extended, the width of the extended wall is approximately 2*W or 2W. It should be realized that if the retractable wall 200, 204, and/or 208 includes n portions each having a width W, then the width of the retractable wall when fully extended is approximately n*W or nW.

In one embodiment, when the gamma cameras 20 and 22 are configured in the L-mode configuration shown in FIGS. 1A and 1B, the retractable walls 200, 204, and 208 are fully retracted into the respective recesses such that an outer edge 222 of each retractable wall 200, 204, and 208 is substantially flush or level with the detecting face 128. In the L-mode configuration, the gamma cameras 20 and 22 may be repositioned without interference from the retractable walls 200, 204, and 208. In the H-mode configuration shown in FIG. 6, at least some of the retractable walls 202, 204, and/or 208 are at least partially extended. As shown in FIG. 8A, at least some of the retractable walls 202, 204, and/or 208, when fully extended, form a substantially square or rectangular anatomy capture region 230. The anatomy capture region 230 is selectively sized to receive the anatomy of interest 24 therein. For example, the size of the anatomy capture region 230 may be increased to facilitate imaging a larger anatomy of interest by repositioning the gamma cameras 20 and 22 and at least some of the retractable walls 202, 204, and/or 208 may be more fully extended to form a larger anatomy capture region 230 to facilitate imaging a more dense or larger anatomy of interest 24. Moreover, to facilitate imaging a smaller anatomy of interest 24, the gamma cameras 20 and 22 and at least some of the retractable walls 202, 204, and/or 208 may be partially retracted into the housing 110 to form a smaller anatomy capture region 230 to facilitate imaging a smaller anatomy of interest 24.

Referring again to FIGS. 9A and 9B, in one embodiment, the retractable walls 202, 204, and/or 208 are extended or retracted utilizing a manual lever 232. Optionally, the retractable walls 202, 204, and/or 208 may be extended or retracted utilizing a spring mechanism (not shown). Although, the retractable walls 202, 204, and/or 208 are illustrated as telescoping walls, it should be realized that the retractable walls 202, 204, and/or 208 may also be embodied as detachable walls or fixed walls. Moreover, the retractable walls 202, 204, and/or 208 may be embodied as folding walls or otherwise collapsing and adjusting walls. As such, the retractable walls 202, 204, and/or 208 form self-adjusting or adjustable side walls that facilitate restraining the anatomy of interest 24 in front of active area of the gamma cameras 20 and 22 when the molecular imaging system is configured in the H-mode mode.

Figure 10A:
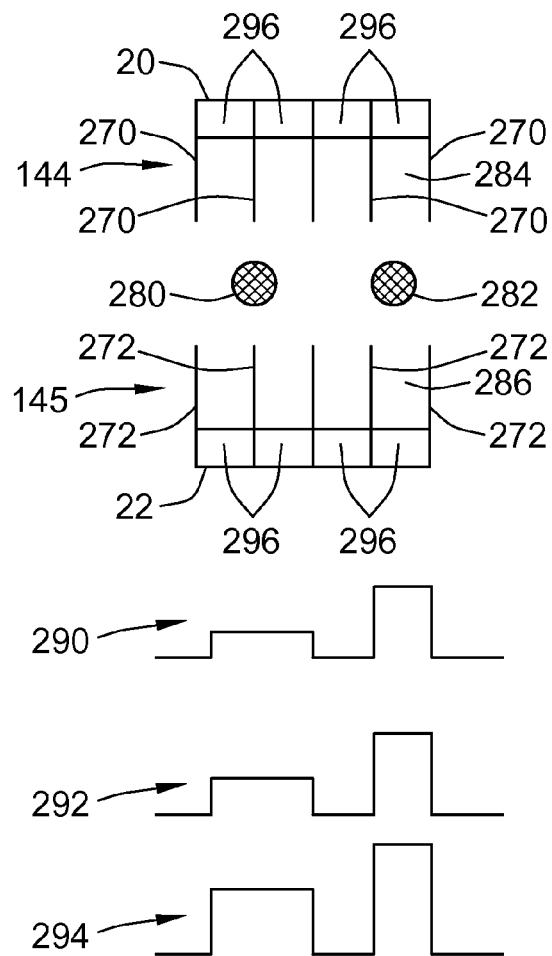
FIG. 10A is a schematic illustration of a first exemplary collimator alignment.
Figure 10B:
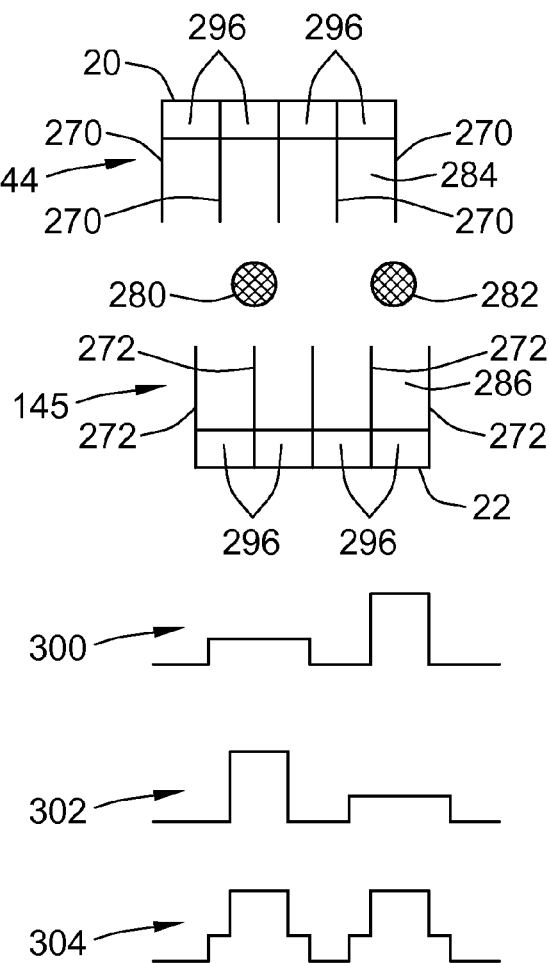
FIG. 10B is a schematic illustration of a second exemplary collimator alignment.

FIG. 10A is schematic illustration of a portion of the gamma cameras 20 and 22 in a first alignment. FIG. 10B is schematic illustration of a portion of the gamma cameras 20 and 22 in a second alignment. As discussed above, each gamma camera 20 and 22 may generate a single image that is viewable by the operator. Specifically, the two images may be side-to-side images, images at forty-five degree angles, or top and bottom images, for example. To facilitate generating a single combined image from the two images, the gamma camera 20 is positioned in a known alignment with respect to gamma camera 22.

Therefore FIG. 10A illustrates a cross-section of the collimators 144 and 145 arranged in a first operational alignment and FIG. 10B illustrates a cross-section of the collimators 144 and 145, and thus gamma cameras 20 and 22 in a second operational alignment. As discussed above, the gamma cameras 20 and 22 are adjustable to perform imaging in both an L-mode configuration and an H-mode configuration. Moreover, each gamma camera 20 and 22 may be separately aligned within each configuration. More specifically, the gamma camera 20 may be offset from the gamma camera 22 in the X, Y, and/or Z direction while still maintaining the gamma cameras 20 and 22 in the L-mode or H-mode configuration. In the exemplary embodiment, the collimator 144 is substantially aligned with the second collimator 145. Moreover, the first and second collimators 144 and 145 each have a resolution that is approximately 5 millimeters at one-half mean breast thickness.

Referring again to FIG. 10A, the gamma camera 20, and thus collimator 144 is approximately aligned with the gamma camera 22, and thus collimator 145, in the Z-direction. More specifically, in this embodiment, the septa 270 of collimator 144 are aligned with the septa 272 of the collimator 145. In this configuration, the line of sight of the collimator 144 is collinear with the line of sight of the collimator 145 such that the septa 270 and 272 are substantially perfectly aligned. As shown in FIG. 10A, one lesion 280 is substantially disposed between two septa, whereas a second lesion 282 is disposed between two holes 284 and 286 defined by the septa. In this case, the signal 290 output from the gamma camera 20 is combined with the signal 292 output from the gamma camera 22 to form a combined signal 294. The combined signal 294 of the first lesion 280 represents the total response from both gamma cameras 20 and 22 and is spread out over two pixels 296, e.g. the response is wide and flat. Whereas the combined signal 294 of the second lesion 282 has a doubled response in half the pixels 296, therefore the combined signal of the second lesion 282 is aliased, e.g. there is a phase mismatch between the frequency of the lesion 282 and the frequency of the gamma cameras.

In another alignment configuration, shown in FIG. 10B, the gamma camera 20, and thus collimator 144 is offset from the gamma camera 22, and thus collimator 145, by approximately ½ pixel. More specifically, the gamma cameras 20 and 22 are aligned such that the lesion 280 is positioned between an opening 284 on the collimator 144 and a septa 272 in the collimator 145. Moreover, the lesion 282 is positioned between an opening 286 on the collimator 144 and a septa 272 in the collimator 144. During operation, the lines of sight of the collimators 144 and 145 are ½ pixel displaced in an x-direction, a y-direction, or both an x and y direction. In this case, a signal 300 output from the gamma camera 20 is combined with a signal 302 output from the gamma camera 22 to form a combined signal 304. In this case, the combined signal 304, generated by addition of the two images of the lesions, substantially equalizes the translation dependent MTF & DQE of the pixelated detector and produces a doubling of the effective Nyquist frequency of the single gamma cameras by themselves. Thus the dual gamma camera system of 2.5 mm pixels functions similar to a system of 1.25 mm pixels. In the exemplary embodiment, to optimize scan time without sacrificing detection ability, the far field resolution limit of the collimators is adjusted by adjusting the collimator height to 2.1 cm or the collimator aspect ratio to 10.

Figure 11:
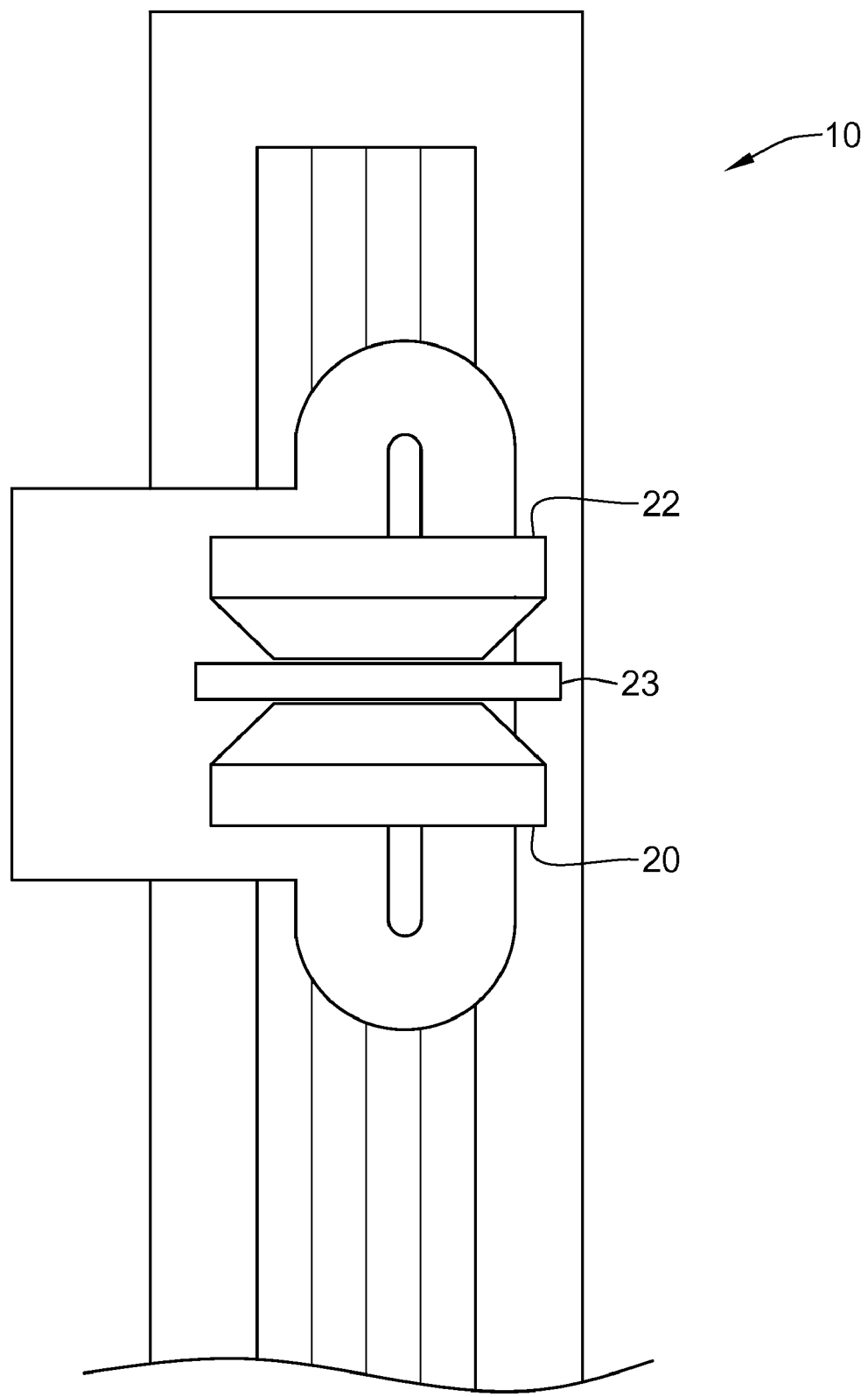
FIG. 11 is a front view of an exemplary calibration position.

FIG. 11 is a side view of the imaging system configured to perform calibration. As shown in FIG. 11, the gamma camera 20 and the gamma camera 22 are positioned in the H-mode. Moreover, a flood source 23 is disposed between the gamma cameras. During operation, the flood source is activated to perform to transmit light through the detector collimators to calibrate the gamma cameras. In this manner, the extrinsic calibration to verify the energy and sensitivity of each gamma camera is defined.

In various embodiments, the molecular imaging system 10, shown above is provided by a method that includes positioning a pair of gamma cameras in an L-mode imaging configuration. A radiopharmaceutical may then be injected into a patient and thereby into an anatomy of interest. Optionally, the radiopharmaceutical may be injected prior to positioning the anatomy of interest or prior to positioning the gamma cameras. The anatomy of interest is then immobilized between the pair of gamma detectors. As discussed above, in the L-mode configuration, the anatomy of interest rests on the gamma detectors. Moreover, an immobilization force may be applied to the anatomy of interest to facilitate retaining the anatomy of interest in a substantially fixed position during the imaging procedure. An imaging scan of the anatomy of interest is then performed on the anatomy of interest immobilized between the pair of gamma detectors.

The imaging operation results in a first image being generated by the first gamma camera and a different second image being generated by the second gamma camera. In the exemplary embodiment, the method also includes combining the first and second image to form a combined image. One method of generating a combined image includes registering the first gamma camera image with the second gamma camera image. Registration may include locating a lesion on the first image and aligning the collimator on the first gamma camera with a different second collimator on the second gamma camera such that the lesion is located between either a pair of holes or a pair of septa on the collimators, e.g. the two collimators are perfectly aligned. The resultant registered images may then be combined by addition, geometric mean, error-weighted mean, or another algorithm to form the combined image. Optionally, registration may include locating a lesion on the first image and aligning the collimator on the first gamma camera with a different second collimator on the second gamma camera such that the lesion is located between septa on the first collimator and a hole on the second collimator, e.g. the two collimators are offset by ½ pixel. The resultant registered images may then be combined to form the combined image.

Thus, a molecular imaging system is provided, for example, configured as an upright stand-alone breast imaging system. The molecular imaging system includes two gamma cameras that are each adapted to render it superior performance for breast cancer management. The gamma cameras are sensitive in their field of view to the gamma rays emitted from the anatomy of interest and form an image of the areas of concentration of an imaging agent. The gamma camera has reduced insensitive edges around the field of view, reduced thickness, chamfers, and limited resolution collimators disposed to increase the sensitivity of imaging. The imaging system described herein therefore reduces background noise, reduces acquisition time, and improves the limits of cancer lesion detection. More specifically, the molecular imaging system described herein may be configured in an L-mode configuration for performing 3D localization and biopsy of an anatomy of interest. The molecular imaging system may also be configured in the H-mode configuration. In the H-mode configuration adjustable or retractable retaining device or walls may be utilized to correct positioning errors for improved lesion detection. Moreover, the gamma cameras include chamfered edges to improve L-mode visibility and decrease patient discomfort. The edges of the camera in contact with the patient are rounded and or covered with foam to avoid injury to the patient.

While the invention has been described in terms of various specific embodiments, those skilled in the art will recognize that the invention can be practiced with modification within the spirit and scope of the claims.

What is claimed is:

1. A gamma camera comprising:
   a housing
   a cadmium zinc telluride (CZT) camera disposed within the housing, and
   at least one retractable wall coupled to the housing and adapted to secure an anatomy of interest in a field-of-view of the gamma camera.

2. The gamma camera of claim 1 wherein the housing comprises a chamfered edge to enable the gamma camera to contact a second gamma camera when the gamma camera is positioned in an L-mode imaging configuration.

3. The gamma camera of claim 1 wherein the housing comprises a second chamfered edge that is formed on an opposite side of the housing from the chamfered edge.

4. The gamma camera of claim 1 wherein the housing comprises a lower surface, an upper surface, and a centerline disposed between the upper and lower surfaces, the a chamfered edge extending from the centerline to the upper surface.

5. The gamma camera of claim 1 wherein the housing comprises a second chamfered surface extending from the centerline to the lower surface.

6. The gamma camera of claim 1 wherein the housing comprises a detecting surface and an opening extending through the detecting surface, the retractable wall configured to extend through the opening.

7. The gamma camera of claim 1 further comprising a second retractable wall coupled to the housing and adapted to secure an anatomy of interest in the field-of-view of the gamma camera.

8. The gamma camera of claim 1 further comprising a different second retractable wall coupled to the housing, the second retractable wall being positioned perpendicular to the retractable wall and configured to be fully retracted into the housing in a first imaging mode and extend from the housing in a different second imaging mode.

9. The gamma camera of claim 1 wherein the cadmium zinc telluride (CZT) camera comprises a pixilated solid state detector.

10. The gamma camera of claim 1 wherein the housing comprises a first side, a second side disposed opposite to the first side, a third side, a fourth side, the first and second sides comprising a chamfered surface to enable the gamma camera to contact a second gamma camera.

11. The gamma camera of claim 1 further comprising a collimator including a plurality of holes, each collimator hole being registered with a respective pixel formed on the CZT detector.

12. The gamma camera of claim 1 further comprising a manual lever coupled to the retractable wall and configured to extend and retract the retractable wall.

13. The gamma camera of claim 1 wherein the cadmium zinc telluride (CZT) camera comprises a solid state detector, an electronics device coupled to the solid state detector, and a collimator disposed on the solid state detector.

14. A gamma camera comprising:
   a housing comprising a chamfered edge to enable the gamma camera to contact a different second gamma camera when the gamma camera is positioned in an L-mode imaging configuration;
   a cadmium zinc telluride (CZT) camera disposed within the housing, and
   at least one retractable wall coupled to the housing and adapted to secure an anatomy of interest in a field-of-view of the gamma camera.

15. The gamma camera of claim 14 wherein the housing comprises a second chamfered edge that is formed on an opposite side of the housing from the chamfered edge, the chamfered edge and the second chamfered edge each extending from a centerline disposed between an upper and lower surface of the housing to the housing upper surface.

16. The gamma camera of claim 14 further comprising a different second retractable wall coupled to the housing, the second retractable wall being positioned perpendicular to the retractable wall and configured to be fully retracted into the housing in a first imaging mode and extend from the housing in a different second imaging mode.

17. A method of fabricating a gamma camera, said method comprising:
   fabricating a housing that includes a first side, a second side, a third side, a fourth side, and an opening defined by the first, second, third, and fourth sides;

installing a cadmium zinc telluride (CZT) camera within the housing opening, and installing at least one retractable wall within the housing, the retractable wall adapted to secure an anatomy of interest in a field-of-view of the gamma camera.

18. The method of claim 17 further comprising chamfering at least one of the housing sides to enable the gamma camera to contact a second gamma camera when the gamma camera is positioned in an L-mode imaging configuration.

19. The method of claim 17 further comprising fabricating the housing to include a recess that is formed between an interior surface of the housing and the CTZ camera, the retractable wall being configured to be stored in the recess in a first mode of operation and extend from the recess in a different second mode of operation.

20. The method of claim 17 further comprising installing a retractable wall including a plurality of telescoping portions within the housing, the retractable wall adapted to telescope from the housing to secure an anatomy of interest in a field-of-view of the gamma camera.

* * * * *